US010828322B1

(12) United States Patent
Ko et al.

(10) Patent No.: US 10,828,322 B1
(45) Date of Patent: Nov. 10, 2020

(54) MOLECULARLY IMPRINTED POLYMERS FOR SEQUESTERING ACETATE AND OTHER MOLECULES

(71) Applicant: CLAVES LIFE SCIENCES LIMITED, Hong Kong (HK)

(72) Inventors: Chi Chiu Ko, Hong Kong (HK); Wai Yip Thomas Lee, Hong Kong (HK); Chung Sing Daniel Poon, Hong Kong (HK); Ka Lun Lai, Hong Kong (HK)

(73) Assignee: CLAVES LIFE SCIENCES LIMITED, Hong Kong (HK)

( * ) Notice: Subject to any disclaimer, the term of this patent is extended or adjusted under 35 U.S.C. 154(b) by 0 days.

(21) Appl. No.: 16/699,173

(22) Filed: Nov. 29, 2019

(51) Int. Cl.
*A61K 31/785* (2006.01)
*C08F 220/56* (2006.01)

(52) U.S. Cl.
CPC .......... *A61K 31/785* (2013.01); *C08F 220/56* (2013.01)

(58) Field of Classification Search
CPC .................................................. B01D 15/3852
See application file for complete search history.

(56) References Cited

U.S. PATENT DOCUMENTS

| | | | |
|---|---|---|---|
| 6,379,599 B1 | 4/2002 | Vaidya et al. | |
| 6,638,498 B2 * | 10/2003 | Green | A61K 31/785 424/164.1 |
| 7,678,870 B2 | 6/2010 | Southard et al. | |
| 7,799,568 B2 | 9/2010 | Charles, Jr. et al. | |
| 8,287,908 B2 | 10/2012 | Kristensen et al. | |
| 9,149,737 B2 | 10/2015 | Krogh et al. | |
| 9,173,943 B2 | 11/2015 | Hoshino et al. | |
| 9,464,150 B2 | 10/2016 | Hall | |
| 9,504,988 B1 | 11/2016 | Gluckman et al. | |
| 10,053,531 B2 | 8/2018 | Zhang et al. | |
| 2002/0015690 A1 | 2/2002 | Green et al. | |
| 2006/0102556 A1 | 5/2006 | Piletsky et al. | |
| 2009/0068758 A1 * | 3/2009 | Karim | B01J 20/26 436/501 |
| 2009/0281272 A1 * | 11/2009 | Yilmaz | B01J 2/06 528/332 |
| 2012/0052757 A1 | 3/2012 | Hearn et al. | |
| 2012/0270964 A1 | 10/2012 | Piletsky et al. | |
| 2013/0011364 A1 | 1/2013 | Fichert et al. | |

(Continued)

FOREIGN PATENT DOCUMENTS

| | | |
|---|---|---|
| CN | 101864029 A | 10/2010 |
| CN | 102489171 A | 6/2012 |
| CN | 103254364 A | 8/2013 |

(Continued)

OTHER PUBLICATIONS

Machine translation CN108752516A (Year: 2018).*

(Continued)

*Primary Examiner* — Alexandre F Ferre
(74) *Attorney, Agent, or Firm* — Biospark Intellectual Property Law

(57) ABSTRACT

Molecularly imprinted polymers (MIPs) capable of binding acetate and other target molecules, processes for their production, pharmaceutical compositions comprising the MIPs, and methods of using the MIPs and pharmaceutical compositions for binding target molecules and for treating conditions associated with accumulation of acetate and other target molecules.

19 Claims, 19 Drawing Sheets

(56) References Cited

U.S. PATENT DOCUMENTS

2015/0299366 A1* 10/2015 Zhang ................... C08F 2/38
    428/402
2016/0199752 A1* 7/2016 Farr ...................... B01D 15/20
    210/673

FOREIGN PATENT DOCUMENTS

| CN | 103881037 A | | 6/2014 |
|---|---|---|---|
| CN | 104804133 A | | 7/2015 |
| CN | 107216416 A | | 9/2017 |
| CN | 108752516 A | * | 11/2018 |
| WO | 2019/002535 A1 | | 1/2019 |

OTHER PUBLICATIONS

Alshareef, 2017, "Construction and Evaluation of Novel Molecularly Imprinted Polymers (MIPs) Using Helical Poly(3-Methyl-4-Vinylpyridine)," Electronic Theses & Dissertations Collection for Atlanta University & Clark Atlanta University. 104.

Perry et al., 2016, "Acetate mediates a microbiome-brain-β-cell axis to promote metabolic syndrome," Nature 534:213-217.

Sikiti et al., 2014, "Synthesis and characterization of molecularly imprinted polymers for the remediation of PCBs and dioxins in aqueous environments," Journal of Environmental Health Science & Engineering, 12:82.

Tang et al., 2017, "Gut Microbiota in Cardiovascular Health and Disease," Circ Res. 120(7):1183-1196.

* cited by examiner

Functional monomers and crosslinker

Acrylamide NIPA NEA MBA NAAC

Crosslinkers

EGDA DVB

PETA TMPTMA

Template molecules

NaOAc KOAc (ⁿBu₄N)OAc C₆H₅COONa

Initiators

V601 Sodium persulfate Ammonium persulfate

US 10,828,322 B1

MOLECULARLY IMPRINTED POLYMERS FOR SEQUESTERING ACETATE AND OTHER MOLECULES

1. BACKGROUND

The human gastrointestinal (GI) tract contains trillions of microbes forming a complex community that interacts closely with human cells. This biomass of gut microbes, also referred to as microbiota, is metabolically active and produces a diverse array of metabolites. Gut microbe derived metabolites include short-chain fatty acids such as acetate, vitamins, bile acids, cofactors, amino acids derivatives, and other organic molecules. These metabolites mediate the functional roles of gut microbiota and affect physiological processes of both the microbes and the host. Very often, these physiological processes are implicated in disease development. As such, the profile of gut microbiota and their metabolites play a major role in disease development, including digestive diseases as well as systemic diseases. See, e.g., Tang et al., 2017, Circ Res. 120(7):1183-1196. For example, acetate produced by gut microbiota is associated with metabolic syndrome and obesity. See, e.g., Perry et al., 2016, Nature 534:213-217.

Molecularly imprinted polymers (MIPs) are polymers having cavities in the polymer matrix that are complementary to and have affinity for a template molecule. MIPs are typically made by polymerizing functional monomers in the presence of a template molecule that is extracted afterwards, leaving behind the complementary cavities. See, e.g., U.S. Pat. Nos. 6,638,498, 8,287,908, and 9,149,737. While MIPs binding various template molecules have been described in the art, MIPs have not been widely adopted for the treatment of human disease.

Accordingly, there is an unmet need for novel MIPs useful for the treatment of various diseases.

2. SUMMARY

The present disclosure provides molecularly imprinted polymers (MIPs) with novel composition (e.g., MIPs with high functional crosslinker content) and/or characteristics (e.g., MIPs that bind to acetate).

In certain aspects, the present disclosure provides MIPs capable of binding target molecules in the gastrointestinal tract, for example microbiota derived metabolites associated with disease such as acetate.

Accordingly, in one aspect, the present disclosure provides MIPs capable of binding acetate. The acetate binding MIPs typically comprise one or more functional molecules (e.g., one or more functional crosslinkers and/or one or more functional monomers). The acetate-binding MIPs of the disclosure can be made using an acetate template molecule (e.g., potassium acetate or sodium acetate) or, alternatively, the template molecule can be another molecule having a similar size, shape, and/or charge as acetate, for example, another short chain fatty acid or salt thereof.

In other aspects, the present disclosure provides MIPs comprising one or more functional molecules, where a majority (greater than 50%) of the functional molecules (e.g., at least 70%, at least 80%, at least 90%, at least 95% or 100% of the functional molecules) are functional crosslinkers. In some embodiments, 100% of the functional molecules are functional crosslinkers. Without being bound by theory, it is believed that in general, MIPs made from functional crosslinkers instead of functional monomers (or with only a relatively small amount of functional monomers) possess higher rigidity and selectivity towards target molecules (e.g., acetate) compared to MIPs prepared from functional monomers. Again, without being bound by theory, it is believed that the greater selectivity can be attributed to the increased rigidity of the MIPs and their target molecule binding sites.

Further exemplary features of MIPs of the disclosure are described in Sections 4.2 and 4.3, and numbered embodiments 1 to 104, infra.

In another aspect, the disclosure provides preparations comprising populations of MIP particles. Exemplary features of MIP preparations are described in Section 4.4 and numbered embodiments 105 to 133, infra.

In another aspect, the disclosure provides processes for making the MIPs of the disclosure. The processes typically comprise polymerizing and crosslinking a mixture comprising one or more functional molecules (e.g., one or more functional crosslinkers and/or one or more functional monomers) in the presence of one or more template molecules. The polymers can be crosslinked by one or more functional crosslinkers. Alternatively, or in addition, a secondary crosslinker, which is not a functional crosslinker, can be used. Further exemplary features of processes for making a MIP of the disclosure are described in Section 4.2 and numbered embodiments 134 to 209.

In another aspect, the disclosure provides MIPs produced by a process for making a MIP of the disclosure and preparations of such MIPs. Exemplary features of such MIPs and MIP preparations are described in Sections 4.2 and 4.4, and numbered embodiments 210 and 211, infra.

In yet another aspect, the disclosure provides pharmaceutical compositions comprising a MIP of the disclosure and pharmaceutical compositions comprising a MIP preparation of the disclosure. Exemplary features of the pharmaceutical compositions are described in Section 4.4 and numbered embodiments 212 to 226, infra.

In yet another aspect, the disclosure provides therapeutic uses of the MIPs, preparations, and pharmaceutical compositions of the disclosure. The MIPs and pharmaceutical compositions of the disclosure can be used, for example, to sequester a target molecule in the gastrointestinal (GI) tract of a subject administered a MIP binding the target molecule or a pharmaceutical composition comprising a MIP binding the target molecule. The acetate-binding MIPs of the disclosure can be used, for example, to sequester acetate in the GI tract, treat a subject diagnosed with or at risk for a condition associated with acetate, for example, metabolic syndrome or obesity, and to reduce the body weight of a subject. Further features of exemplary therapeutic uses of the MIPs and pharmaceutical compositions of the disclosure are described in Section 4.5 and numbered embodiments 227 to 250, infra.

3. BRIEF DESCRIPTION OF THE FIGURES

Figure 5A:
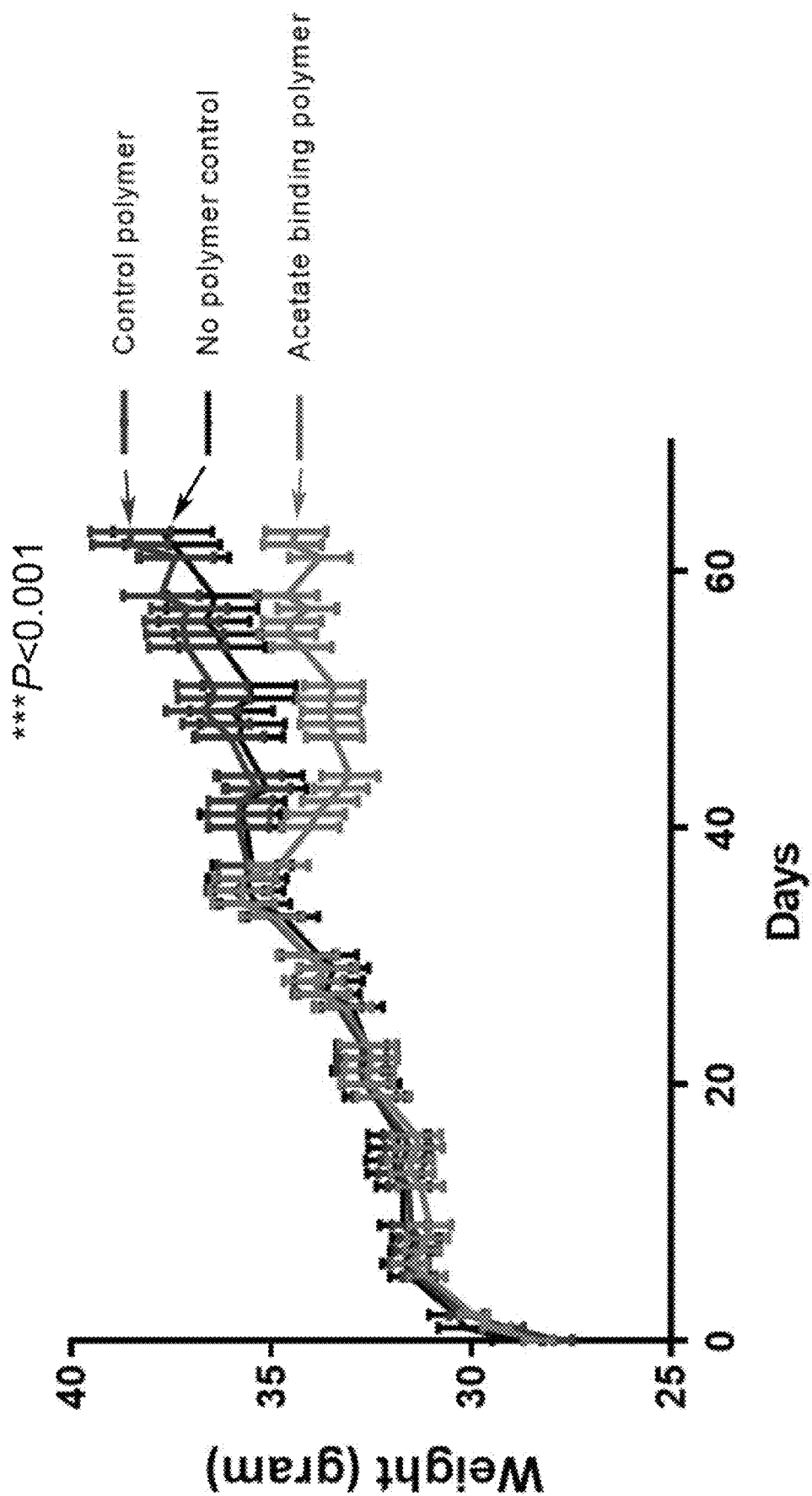
Figure 5B:
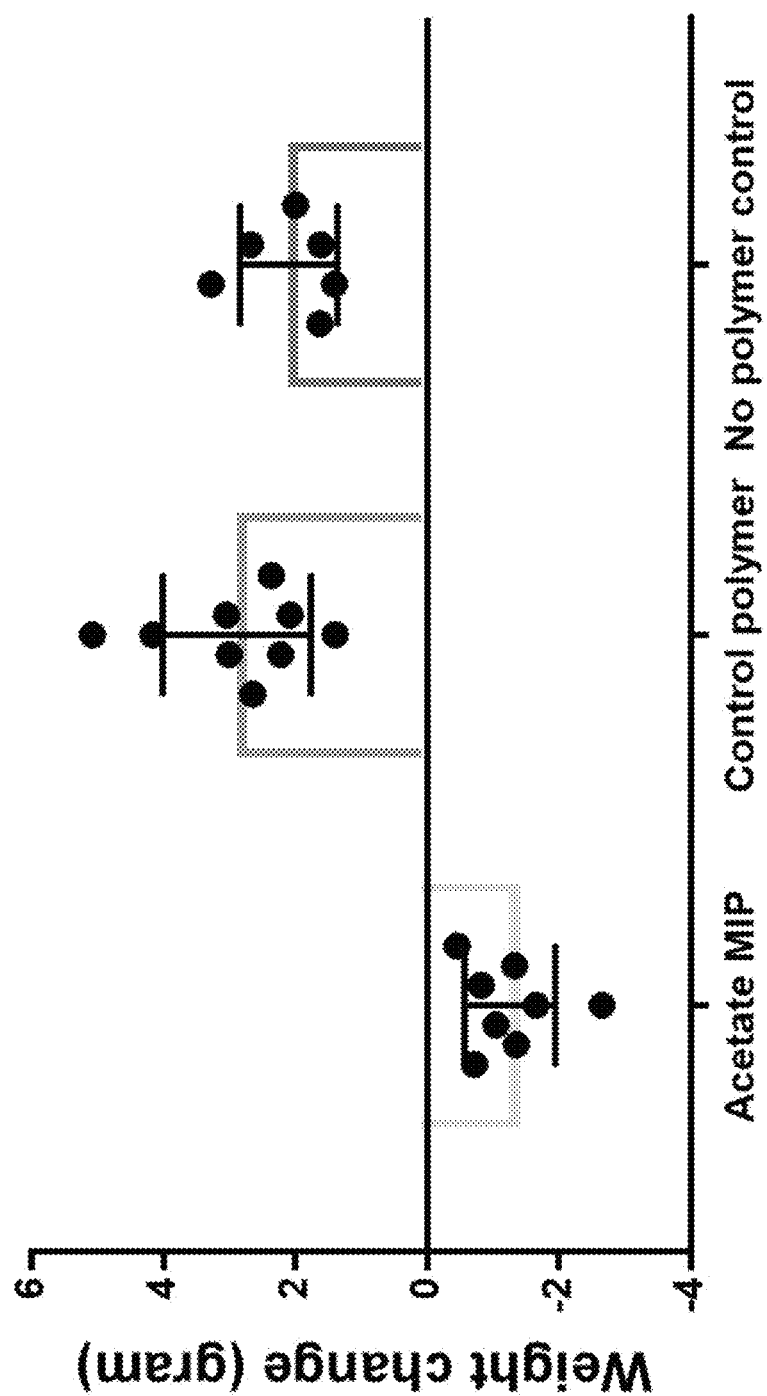
Figure 5C:
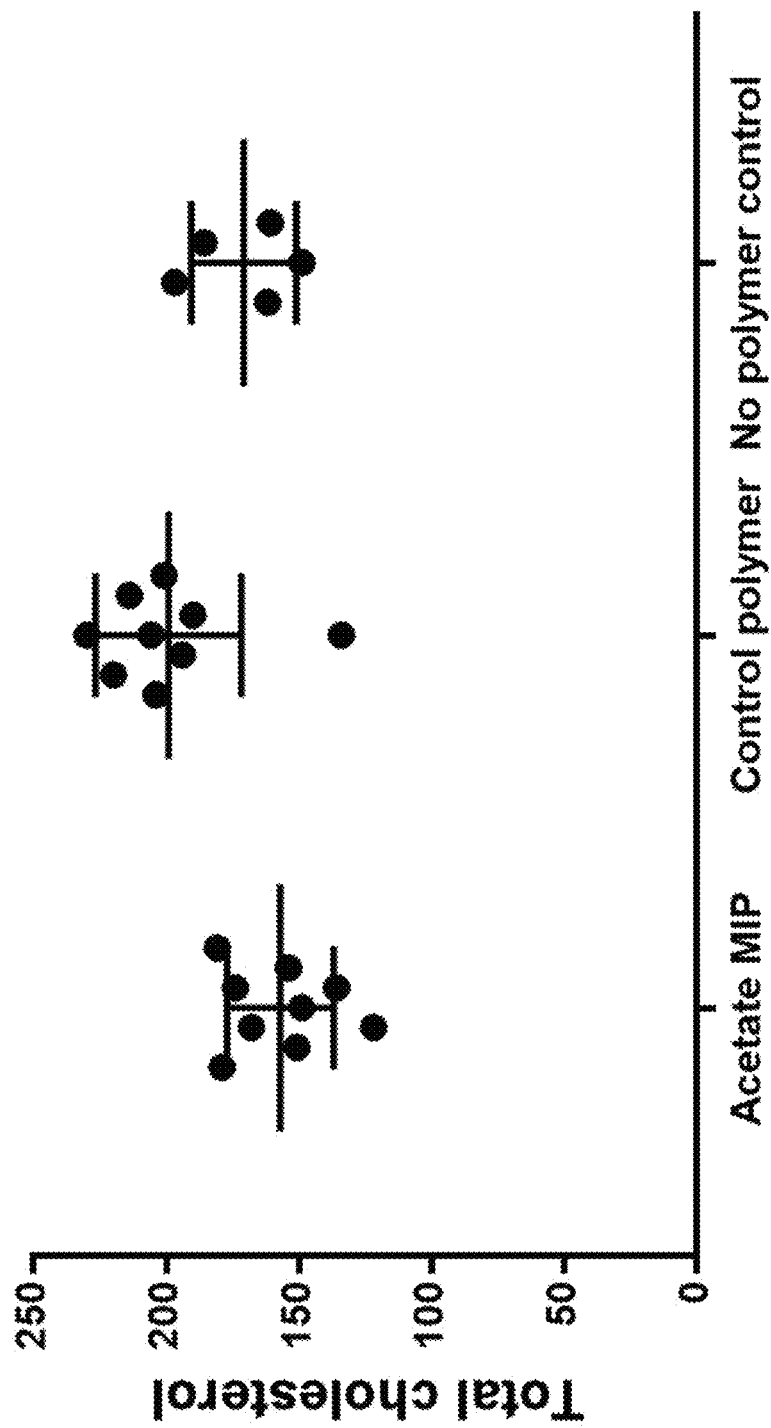
Figure 5D:
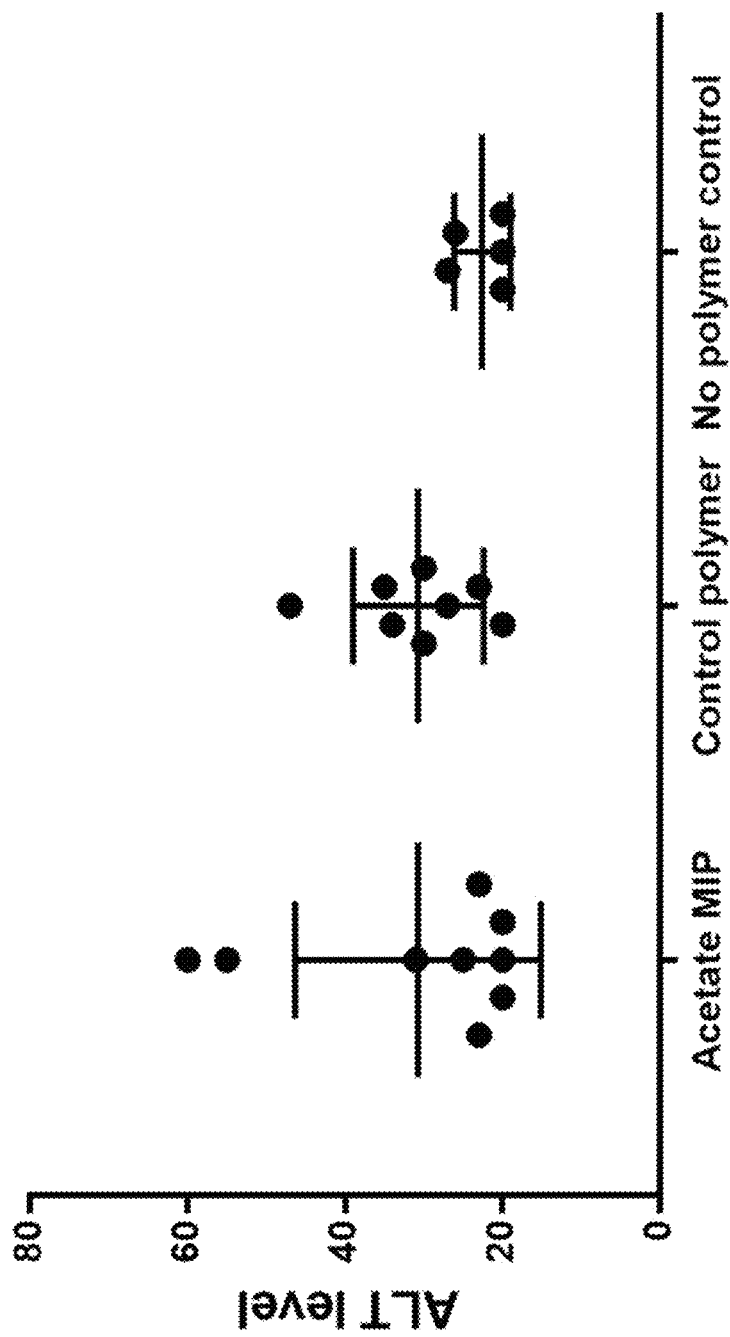
Figure 5E:
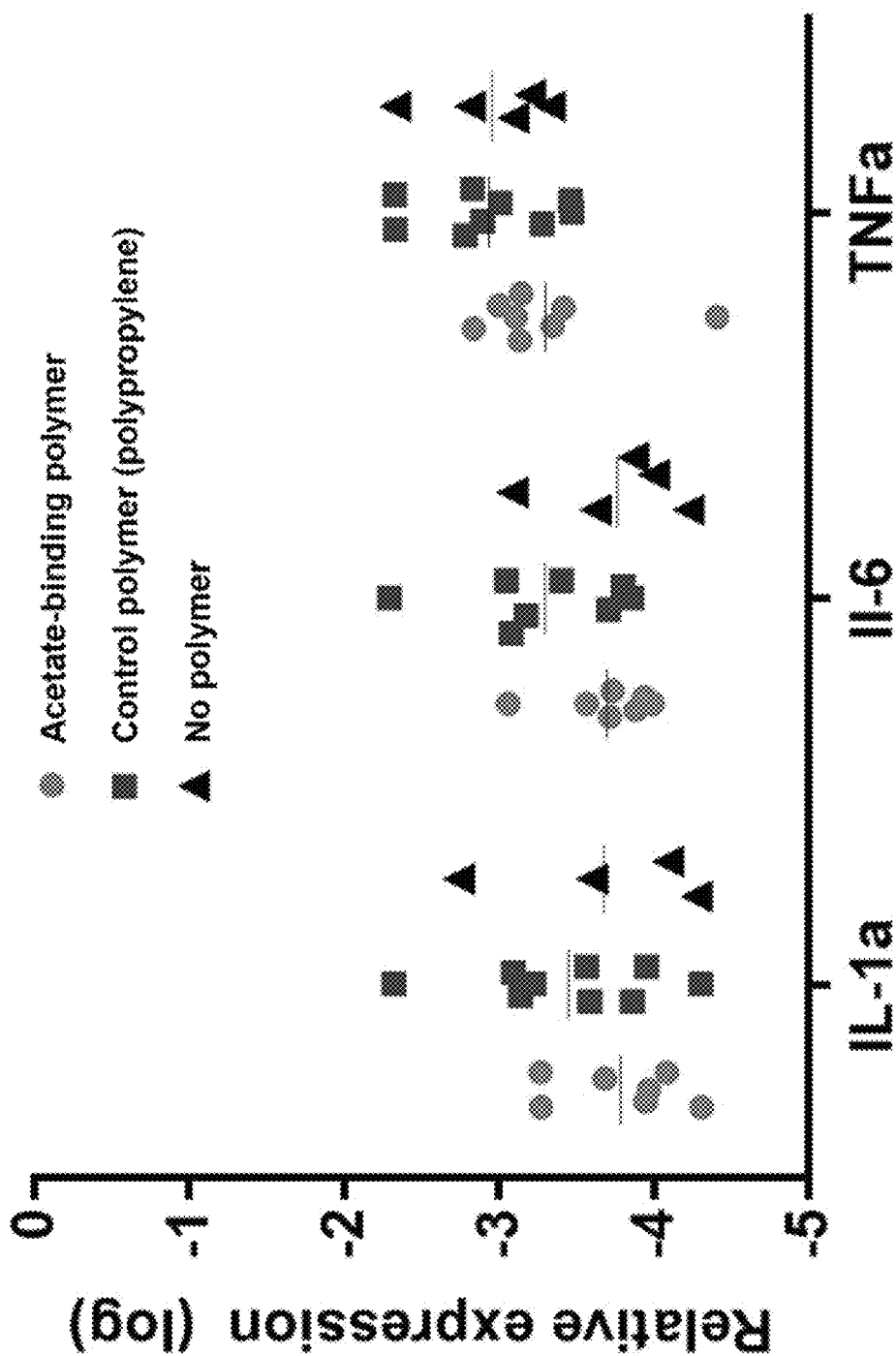
Figure 5F:
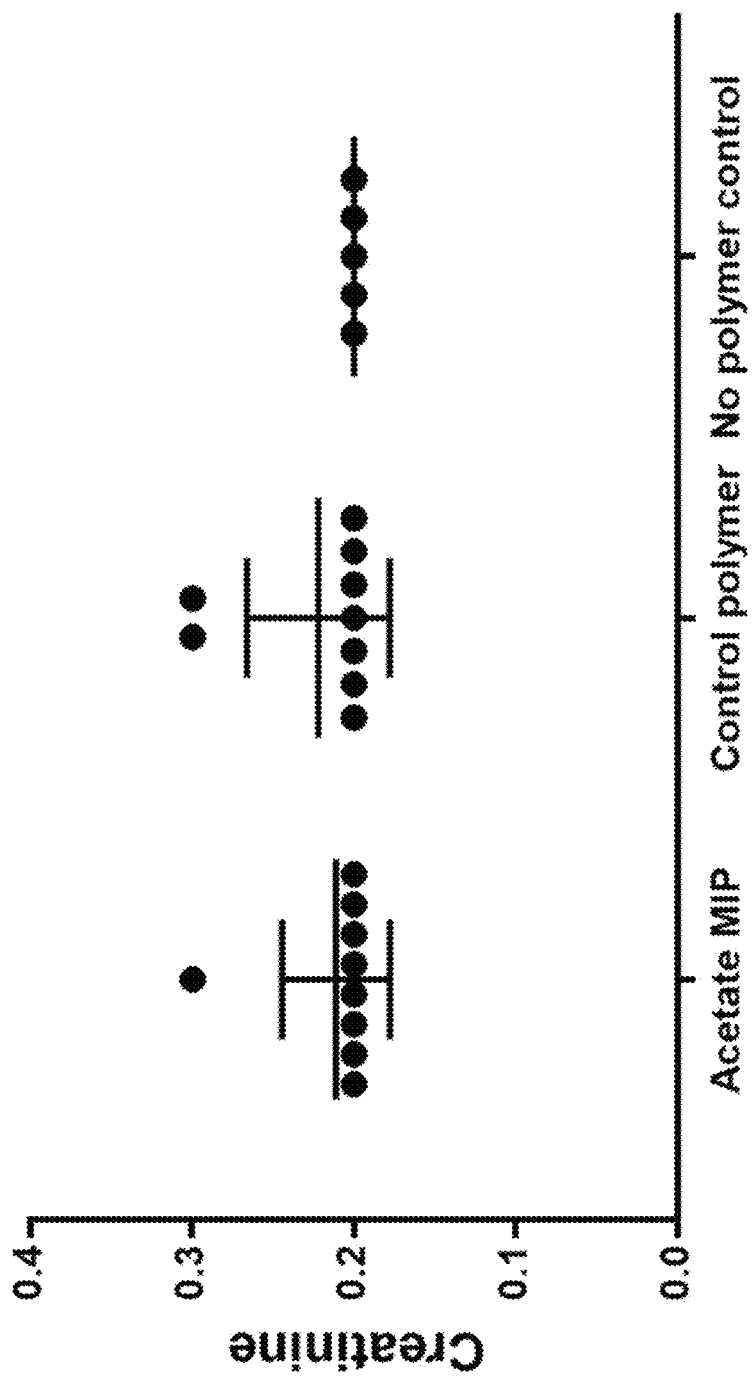

FIGS. 5A-5F show data relating to the safety and efficacy of an acetate-binding MIP in an in vivo study as described in Example 1. FIG. 5A: average body weight of mice in the three groups before and after randomization; FIG. 5B:

change in body weight from the date of randomization to the end of study; FIG. 5C: total cholesterol; FIG. 5D: ALT levels; FIG. 5E: inflammatory gene expression levels; FIG. 5F: creatinine levels.

Figure 6:
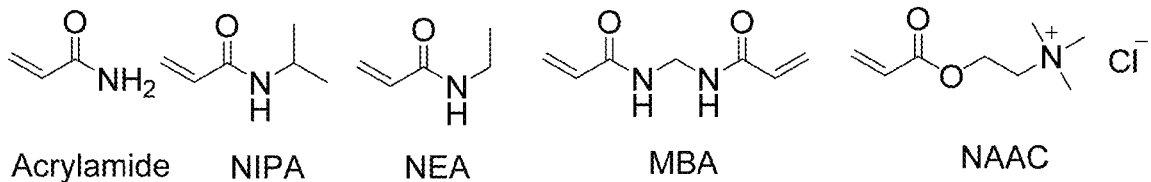
Figure 6:
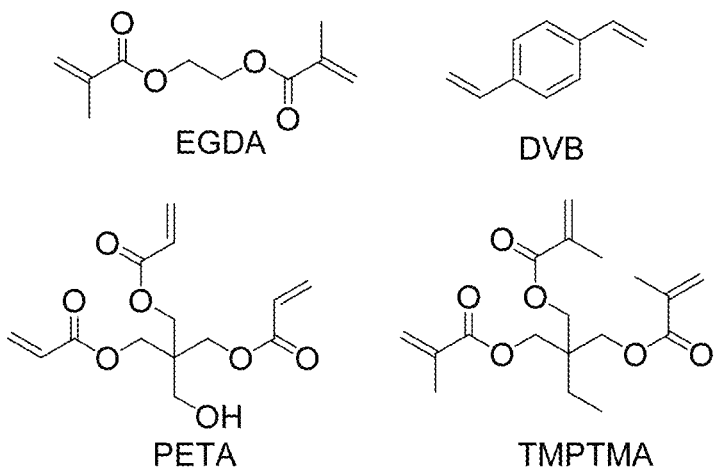
Figure 6:
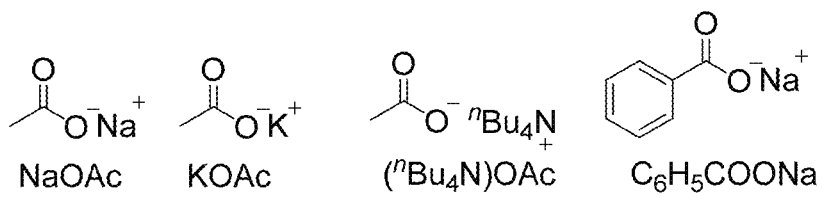
Figure 6:
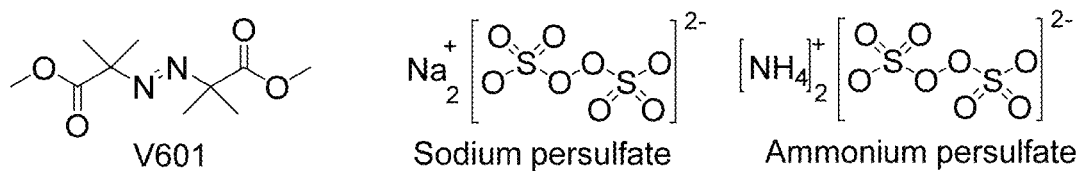

FIG. 6 shows structures of functional monomers, functional crosslinkers, secondary crosslinkers, template molecules, and initiators used to make the MIPs of Example 2.

Figure 7A:
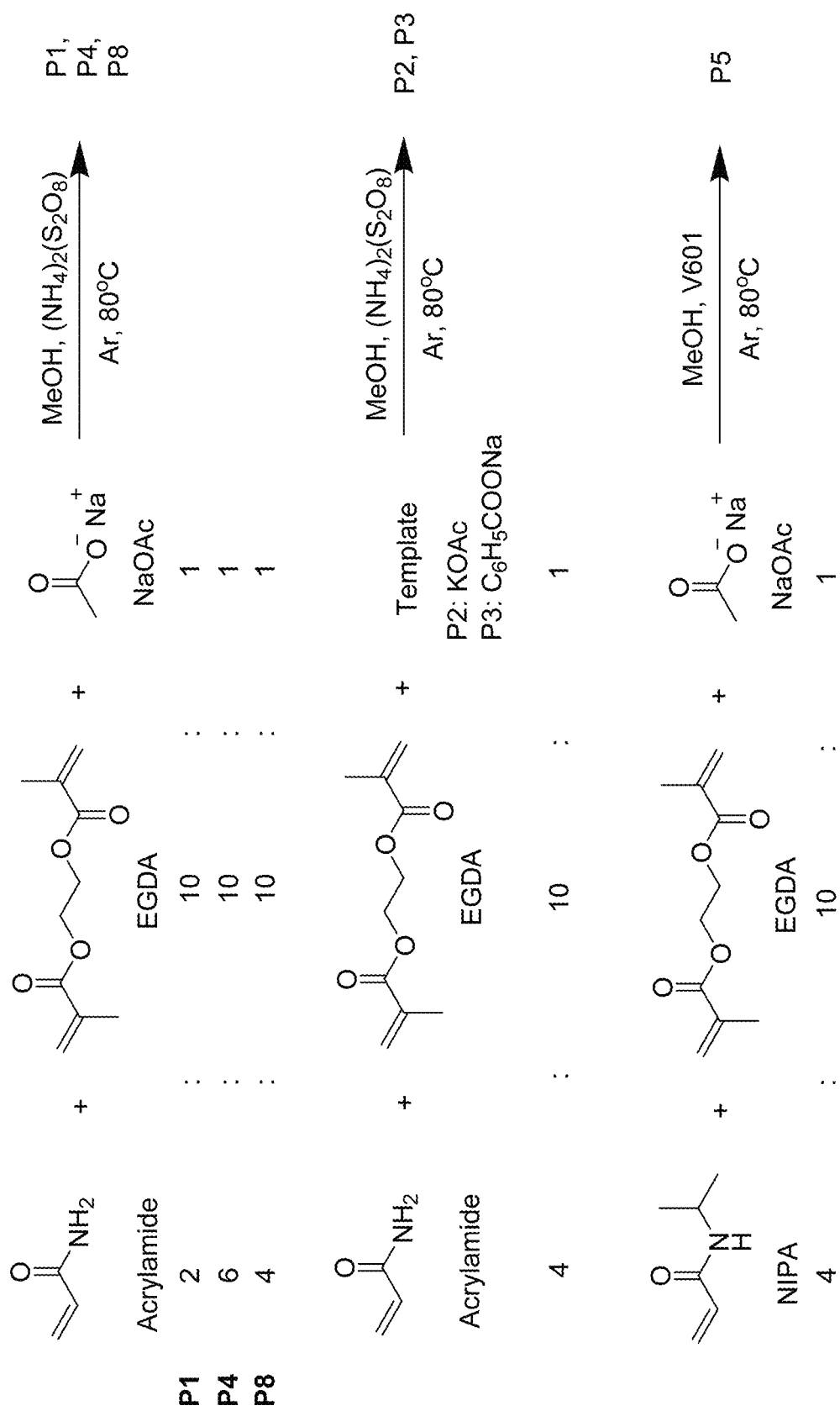
Figure 7B:
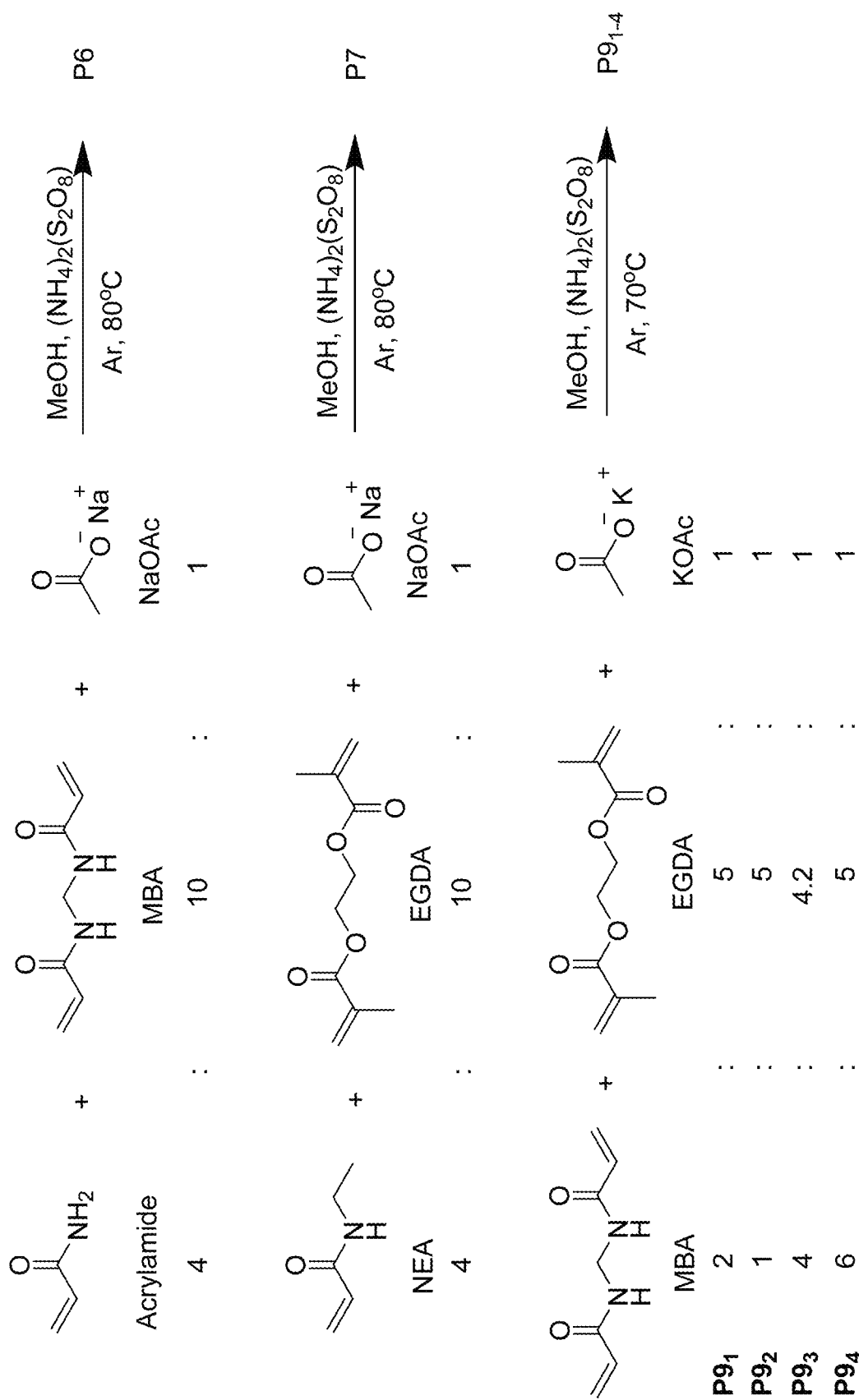

FIGS. 7A-7B show synthetic schemes for acetate-binding MIPs P1-P9. FIG. 7A: P1-P5, P8; FIG. 7B: P6-P7, P9.

Figure 8A:
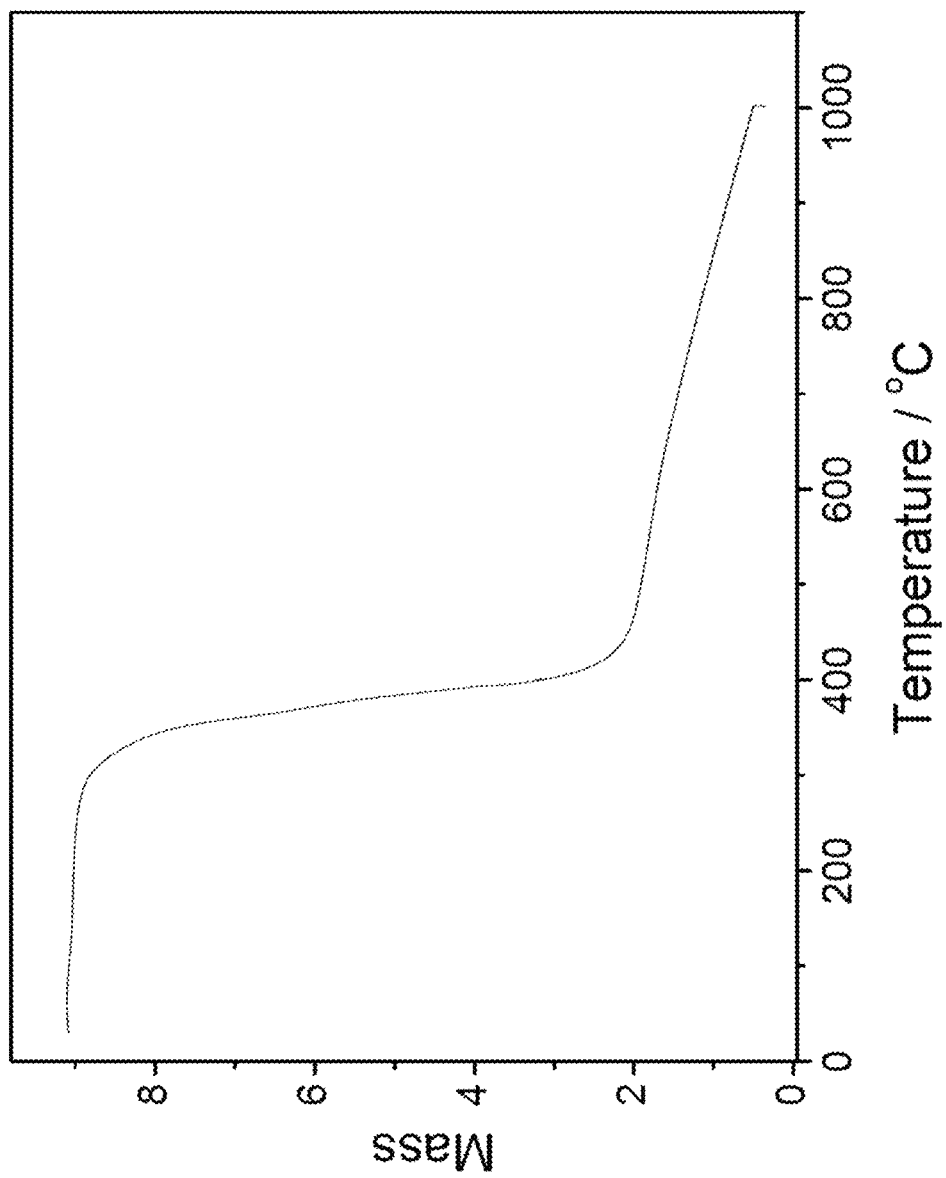
Figure 8B:
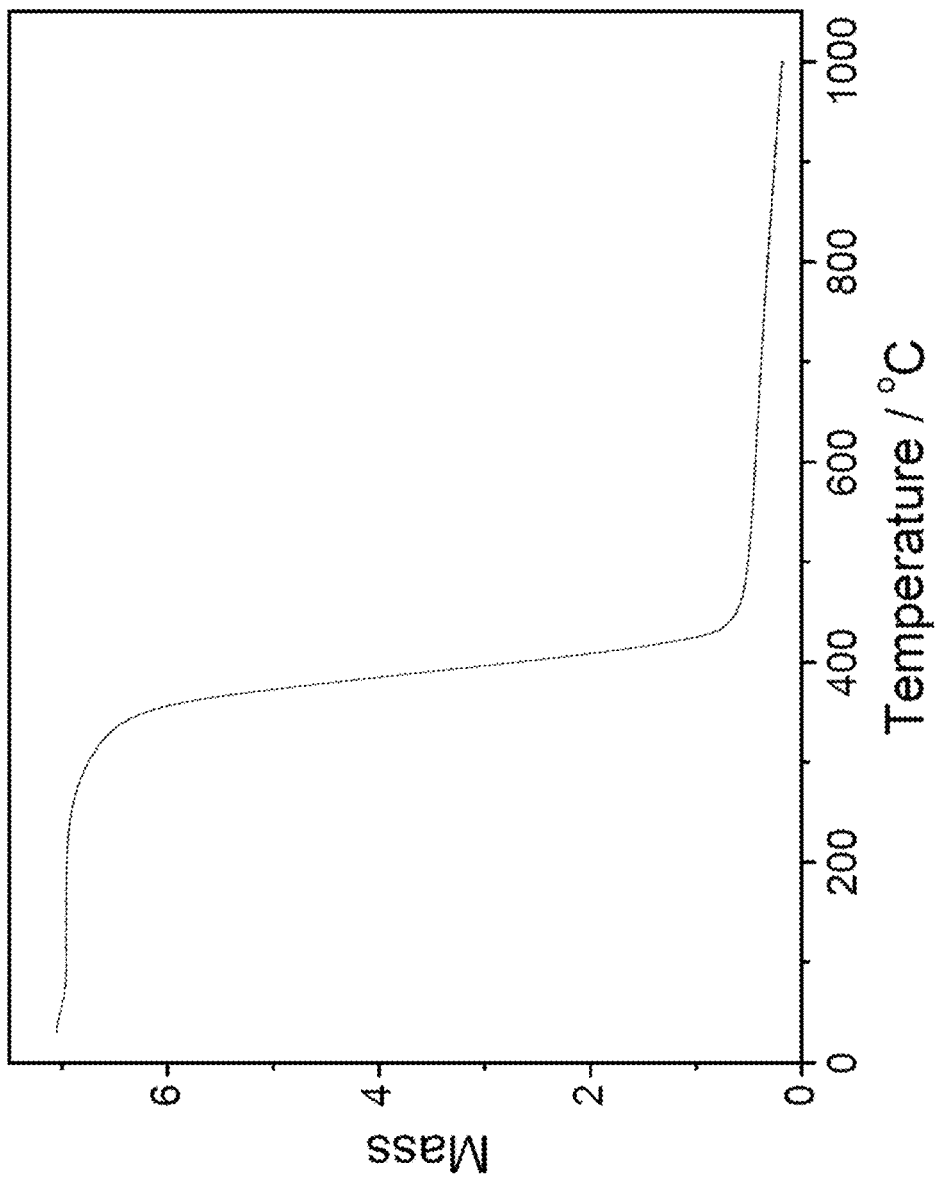
Figure 8C:
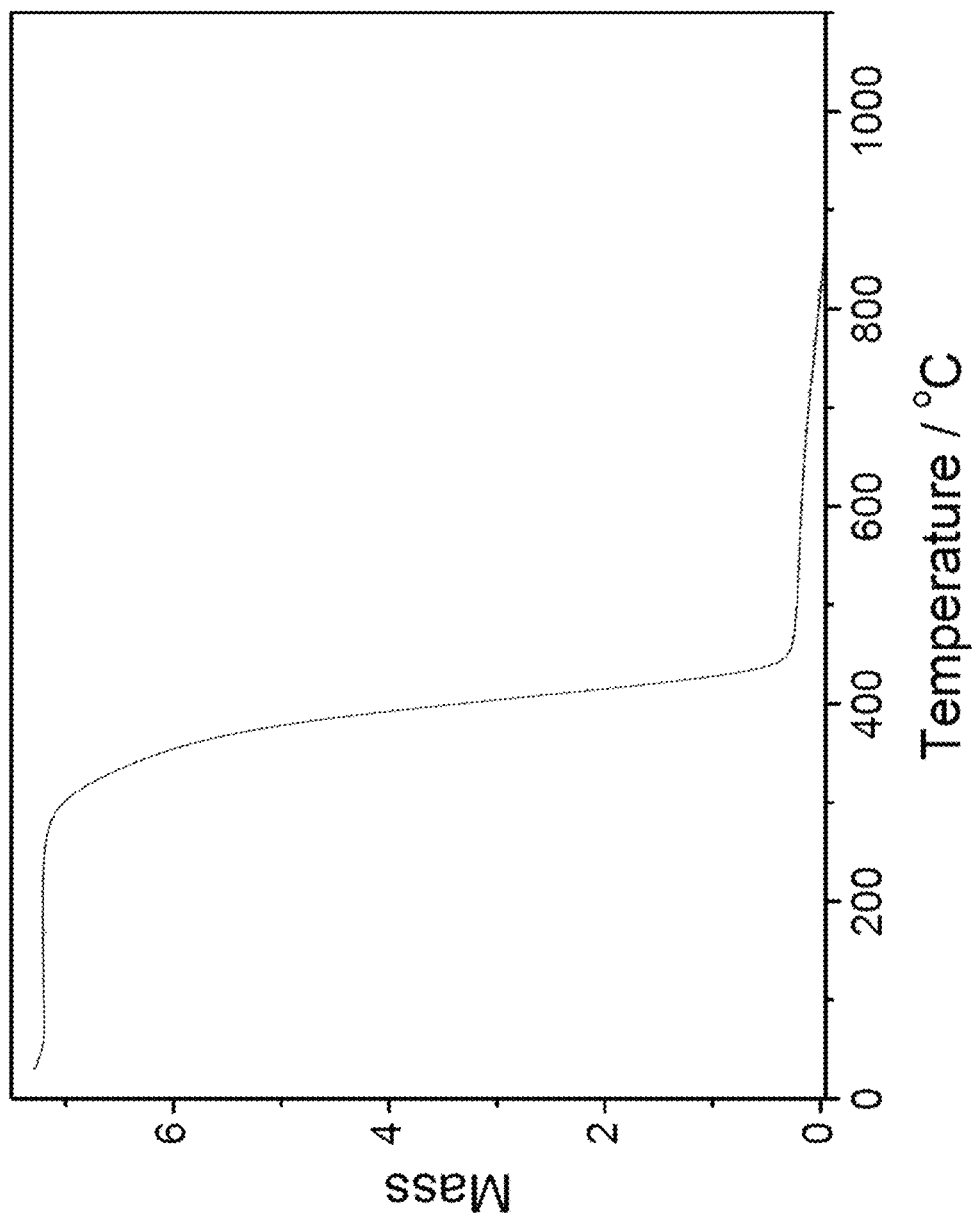

FIGS. 8A-8C show thermograms for acetate-binding MIPs P6 (FIG. 8A), P8 (FIG. 8B), and $P9_L$ (FIG. 8C).

Figure 9:
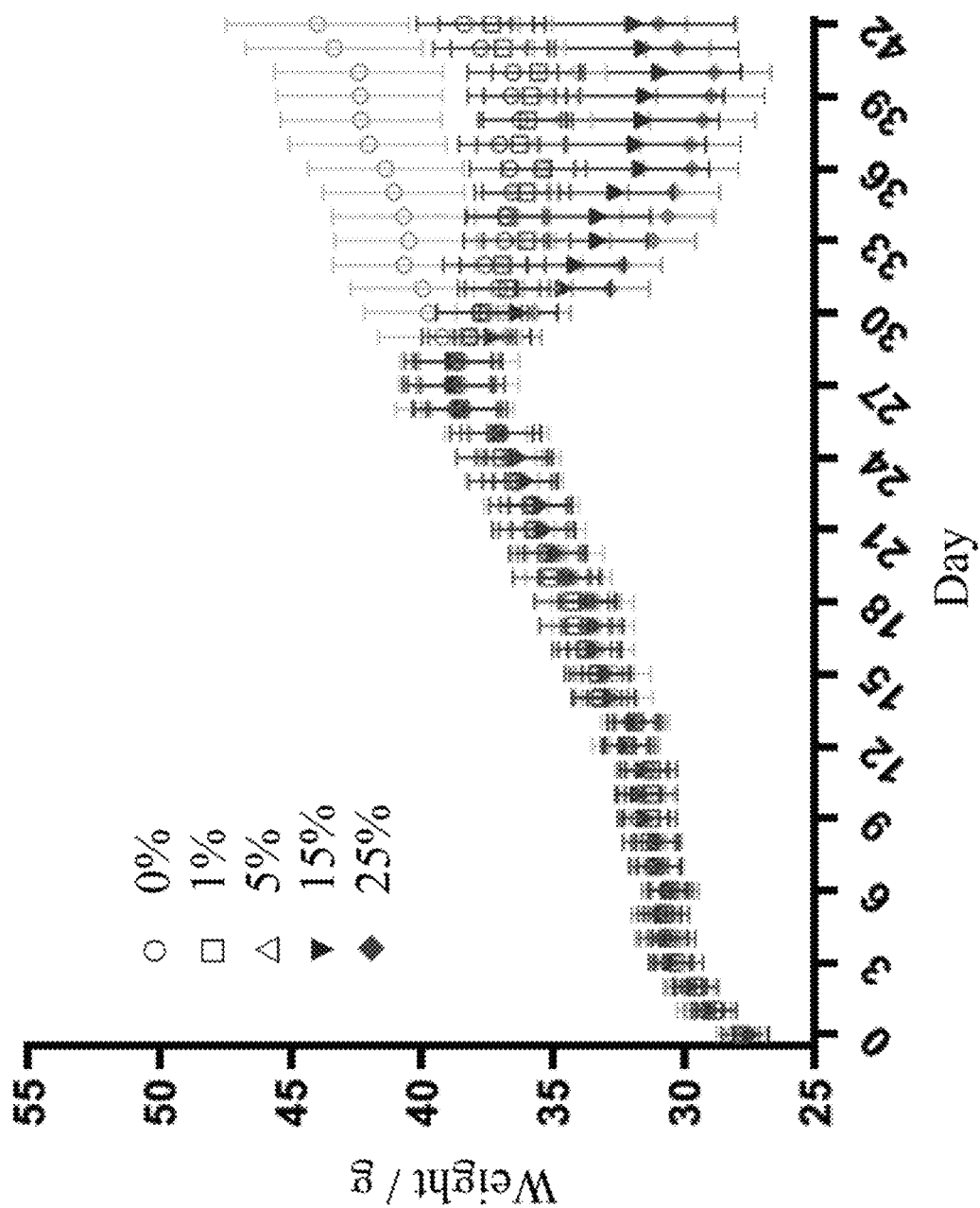

FIG. 9 shows weights of mice administered acetate-binding MIP $P9_L$ in the study of Example 2.

Figure 10:
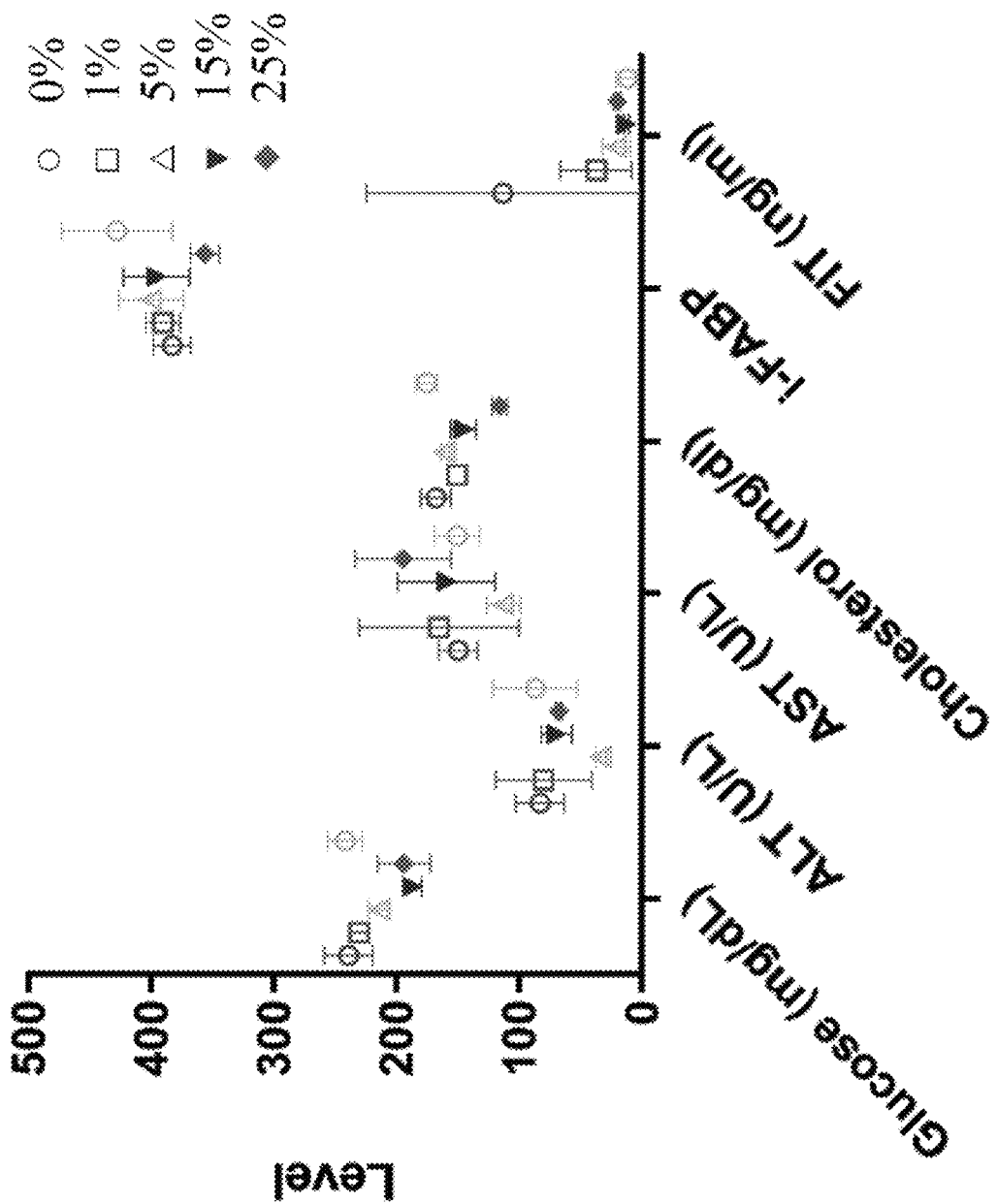

FIG. 10 shows glucose levels, liver enzymes (ALT, AST), lipid (cholesterol), markers of mucosal injury (iFABP, FIT) in mice administered $P9_L$ in the study of Example 2.

Figure 11:
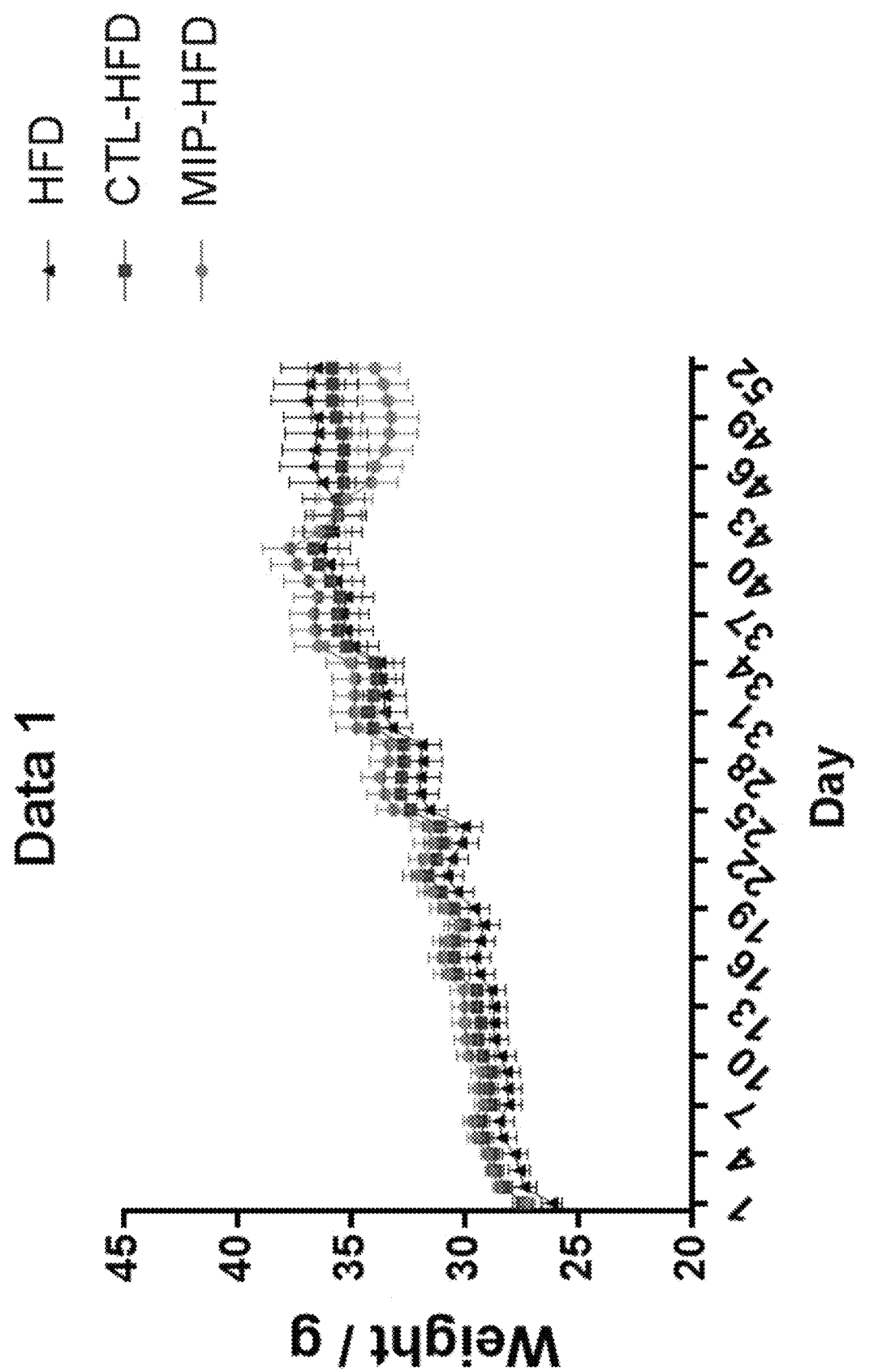

FIG. 11 shows average body weights of mice administered acetate-binding MIP P8.

4. DETAILED DESCRIPTION

4.1. Definitions

As used herein, the following terms are intended to have the following meanings:

Functional Crosslinker: The term "functional crosslinker" as used herein refers to a functional molecule capable of crosslinking two or more polymer chains. Functional crosslinkers can also be capable of extending a polymer chain during a polymerization reaction. Exemplary functional crosslinkers are described in Section 4.2.1.1.

Functional Molecule: The term "functional molecule" as used herein refers to a molecule having one or more groups capable of binding or interacting with a target molecule through a non-covalent interaction (e.g., by hydrogen bonding, ionic bonding, t-t interaction, cation-t interaction, anion-t interaction, van der Waals interactions, or hydrophobic interaction). Exemplary functional groups include amines, amides, carboxyl groups, hydroxyl groups, and aromatic groups. Functional molecules include functional monomers and functional crosslinkers. Exemplary functional molecules are described in Section 4.2.1.

Functional Monomer: The term "functional monomer" as used herein refers to a functional molecule that can extend a polymer chain during a polymerization reaction but not crosslink two or more polymer chains. Exemplary functional monomers are described in Section 4.2.1.2.

Initiator: The term "initiator" as used herein refers to a molecule capable of initiating a polymerization and/or crosslinking reaction. Initiators are known in the art and include thermal initiators and photoinitiators. See, e.g., Myers, T. N. 2002, "Initiators, Free-Radical," Encyclopedia of Polymer Science and Technology, the contents of which are incorporated herein by reference in there entireties. Exemplary initiators are described in Section 4.2.3.

Molecularly Imprinted Polymer ("MIP"): The term "molecularly imprinted polymer" or "MIP" as used herein refers to a crosslinked polymer having cavities complementary to and affinity for a target molecule. An MIP can have affinity for more than one target molecule (e.g., a MIP having affinity for acetate can have affinity for one or more other short chain fatty acids). MIPs of the disclosure typically comprise one or more functional molecules. It should be understood that the expressions "MIP comprising one or more functional molecules," "MIP comprising one or more functional molecules and one or more secondary crosslinkers" and like refer to MIPs into which the one or more functional molecules and one or more secondary crosslinkers (when present) have been incorporated.

Secondary Crosslinker: The term "secondary crosslinker" as used herein refers to a crosslinker that other than a functional crosslinker. A MIP of the disclosure can be prepared with one or more secondary crosslinkers in combination with one or more functional crosslinkers or, alternatively, a MIP of the disclosure can be prepared with one or more secondary crosslinkers without one or more functional crosslinkers. Thus, for the avoidance of doubt, it should be understood that the term "secondary crosslinker" does not imply that a secondary crosslinker is present with or used in combination with any other crosslinker, although in some embodiments one or more secondary crosslinkers are used in combination with one or more functional crosslinkers.

Target Molecule: The term "target molecule" as used herein refers to a molecule (which can be an ion) to which a MIP selectively binds. A target molecule can be a template molecule or an ion of a template molecule used when synthesizing the MIP. A target molecule can also be different from a template molecule used to synthesize the MIP. For example, a target molecule can be a molecule similar in size and/or charge to a template molecule.

Template Molecule: The term "template molecule" as used herein refers to a molecule (which can be an ion) used to molecularly imprint a polymer during MIP synthesis. The term "template molecule" can refer, for example, to an acid, base, or salt used in making a polymerization mixture, as well as corresponding species (e.g., uncharged molecules or ions) which may be present in the polymerization mixture. For example, a polymerization mixture made with potassium acetate may contain non-dissociated potassium acetate as well as dissociated acetate ions.

4.2. Molecularly Imprinted Polymers (MIPs)

The disclosure provides MIPs capable of binding a target molecule, for example acetate. The MIPs of the disclosure typically comprise one or more functional molecules (e.g., one or more functional crosslinkers and/or one or more functional monomers).

Thus, in various aspects, the disclosure provides MIPs comprising (1) one or more functional crosslinkers; (2) one or more functional monomers; or (3) one or more functional crosslinkers and one or more functional monomers. MIPs of the disclosure can include additional components, for example, one or more secondary crosslinkers and/or one or more monomers which are not functional monomers. In some embodiments, the functional molecules and any secondary crosslinkers together comprise 80% or more of the dry weight of the MIP (e.g., 85%, 90%, 95%, 96%, 97%, 98%, 99% or 100%), with the balance (if any) being one or more additional components such as monomers which are not functional monomers and/or residual template molecules. In some embodiments, a MIP of the disclosure comprises one or more functional crosslinkers, one or more secondary crosslinkers, and no or only a small amount of functional monomers (e.g., where less than 20 mol % or less, 15 mol % or less, 10 mol % or less, 5 mol % or less, 4 mol % or less, 3 mol % or less, 2 mol % or less, 1 mol % or less, or 0% of the functional molecules in the MIP are functional monomers). In some embodiments, a MIP of the disclosure comprises one or more functional crosslinkers, one or more secondary crosslinkers, and no functional monomers.

In general, MIPs in the art have been made from functional monomers. However, it has been surprisingly discovered that MIPs made with functional crosslinkers possess unexpectedly superior properties, for example higher target molecule binding capacity, compared to MIPs made with functional monomers. Without being bound by theory, it is believed that MIPs made from functional crosslinkers without functional monomers or with only a relatively small amount of functional monomers (e.g., where 20 mol % or less, 15 mol % or less, 10 mol % or less, 5 mol % or less, 4 mol % or less, 3 mol % or less, 2 mol % or less, 1 mol % or less, or 0% of the functional molecules are functional monomers) possess higher rigidity and selectivity towards target molecules compared to MIPs made with higher amounts of functional monomers. Again, without being bound by theory, it is believed that the greater selectivity can be attributed to the increased rigidity of the MIPs and their target molecule binding sites.

Exemplary functional crosslinkers that can be used in the MIPs of the disclosure are described in Section 4.2.1.1. Exemplary functional monomers that can be used in the MIPs of the disclosure are described in Section 4.2.1.2. One or more secondary crosslinkers can be used to crosslink the polymer in a MIP, either alone or in combination with one or more functional crosslinkers. Exemplary secondary crosslinkers are described in Section 4.2.2. Polymerization of functional monomers and/or functional crosslinkers can be initiated using one or more initiators known in the art, for example, one or more of the initiators described in Section 4.2.3. Exemplary template molecules useful for making a MIP of the disclosure, for example, an acetate-binding MIP, are described in Section 4.2.4. Exemplary MIP synthesis processes are described in Section 4.2.5.

4.2.1. Functional Molecules

Functional molecules include monomers and crosslinkers having one or more groups capable of non-covalent bonding (e.g., by hydrogen bonding, ionic bonding, van der Waals interactions, or hydrophobic bonding) with a target molecule. Exemplary functional groups include amines, amides, carboxyl groups, hydroxyl groups, and aromatic groups.

MIPs of the disclosure can be made from functional crosslinkers, functional monomers, or a combination of functional crosslinkers and functional monomers. A MIP of the disclosure can be made from a single type of functional molecule (e.g., a single functional crosslinker or a single functional monomer) or from a combination of functional molecules (e.g., a combination of two or more functional crosslinkers, a combination of two or more functional monomers, or a combination of one or more functional crosslinkers and one or more functional monomers).

Ratios of functional molecules to crosslinkers (e.g., functional crosslinkers and/or secondary crosslinkers) can range, for example, from 1:5 to 5:1 (e.g., 1:5 to 1:1 or 1:1 to 5:1). For example, the ratio can be 1:5, 1:4, 1:3, 1:2, 1:1, 2:1, 3:1, 4:1, 5:1, 2:5, 3:5, 4:5, 6:5 or any range bounded by any two of the foregoing ratios. In some embodiments, the ratio is 1:5. In other embodiments, the ratio is 2:5. In other embodiments, the ratio is 3:5. In other embodiments, the ratio is 4:5. In other embodiments, the ratio is 6:5. In other embodiments, the ratio is 1:1.

4.2.1.1. Functional Crosslinkers

Exemplary functional crosslinkers that can be used in the preparation of the MIPs of the disclosure (e.g., acetate-binding MIPs) include amide-containing crosslinkers (e.g., N,N'-methylenebis(acrylamide) (MBA)) and urea containing crosslinkers (e.g., 1,3-bis(4-vinylphenyl)urea and 1,3-bis(4-(allyloxy)phenyl)urea, 1,3-diallylurea). In some embodiments, acetate-binding MIPs of the disclosure comprise MBA.

Additional or alternative crosslinkers having one or more groups capable of non-covalent bonding (e.g., by hydrogen bonding, ionic bonding, van der Waals interactions, or hydrophobic bonding) with a given target molecule can be selected by those skilled in the art.

4.2.1.2. Functional Monomers

Exemplary functional monomers that can be used in the preparation of MIPs of the disclosure (e.g., acetate-binding MIPs) include acrylamides, for example, acrylamide (prop-2-enamide), N-alkylacrylamides, and methacrylamides.

Exemplary acrylamides include N-methylacrylamide, N-ethylacrylamide, N-isopropylacrylamide, N-methylmethacrylamide, N-(3-aminopropyl)methacrylamide, N-(2-oxoethyl)-2-acrylamide, and N-(2-aminopyridine)methacrylamide.

Other exemplary functional monomers useful for preparing a MIP (e.g., an acetate-binding MIP) include N-vinylacetamide, N-[[[3-(ethenylsulfonyl)-1-oxopropyl]amino]methyl]-2-propenamide, 4-vinylbenzamide, N-alkyl-(4-vinylbenzamide), N,N'-diethyl(4-vinylphenyl)amidine, a hydroxyl-substituted styrene, an amide-substituted styrene, N-(diaminoethylene)-2-methylprop-2-enamide, N-allylurea, and 1-allyl-2-thiourea.

Additional or alternative monomers having one or more groups capable of non-covalent bonding (e.g., by hydrogen bonding, ionic bonding, van der Waals interactions, or hydrophobic bonding) with a given target molecule during can be selected by those skilled in the art.

4.2.2. Secondary Crosslinkers

Exemplary secondary crosslinkers that can be used in the preparation of MIPs include diallyl derivatives, divinyl derivatives, dimethacrylate derivatives, and bisacrylamide derivatives. Other types of crosslinkers known in the art can also be used.

Exemplary species of secondary crosslinkers that can be used to make a MIP of the disclosure (e.g., an acetate-binding MIP) include ethylene glycol dimethacrylate (EGDA), ethylene glycol diacrylate, 1,2-diallyloxybenzene, divinylbenzene, 1,3-diisopropenylbenzene, divinylsuccinate, 1,3-divinyltetramethyldisiloxane, tri(ethylene glycol) divinyl ether, di(ethylene glycol) divinyl ether, trimethylolpropane trimethacrylate, pentaerythritol triacrylate, and combinations thereof. In some embodiments, acetate-binding MIPs of the disclosure comprise EGDA.

When a secondary crosslinker is used to make a MIP, the molar ratio of the functional molecules (e.g., functional crosslinkers and/or functional molecules) to secondary crosslinkers can be, for example 1:5 to 5:1 (e.g., 1:5 to 1:1 or 1:1 to 5:1). For example, the ratio can be 1:5, 1:4, 1:3, 1:2, 1:1, 2:1, 3:1, 4:1, or 5:1, or any range bounded by any two of the foregoing ratios. In some embodiments, the ratio is 1:1 to 4:5. In some embodiments, the ratio is 1:1.

4.2.3. Initiators

An initiator can be used to initiate polymerization of a mixture comprising one or more functional crosslinkers and/or one or more functional monomers. Polymerization initiators are known in the art and include thermal and photo-radical initiators. Exemplary initiators include potassium persulfate, sodium persulfate, ammonium persulfate, 2,2'-azobis(2-methylpropionate) (V601), 2,2'-azobisisobutyronitrile (AIBN), benzoyl peroxide, t-butyl peroxide, t-butyl hydroperoxide, acetyl peroxide, 2-hydroxy-4'-(2-hydroxyethoxy)-2-methylpropiophenone, benzil derivatives, and other radical initiators reported in Myers, T. N. 2002. "Initiators, Free-Radical," Encyclopedia of Polymer Science and Technology. In some embodiments, processes for making MIPs of the disclosure use a persulfate initiator (e.g., ammonium persulfate).

4.2.4. Template Molecules and Target Molecules

A template molecule used in the synthesis of a MIP can be the same as a desired target molecule, for example a metabolite derived from gut microbiotia or a toxin. For example, the target molecule can be a short chain fatty acid (e.g., acetate), a bile acid, a vitamin, an enzyme cofactor, an amino acid (e.g., phenylalanine), amino acid derivative, or a peptide, and the template molecule can be the same as the target.

Alternatively, a template molecule can be similar to a target molecule in size, shape, charge, or a combination thereof. Thus, for example, an acetate-binding MIP can be made using another short chain fatty acid as template (e.g., propionate, butyrate, or isobutyrate). A non-limiting list of template suitable for the preparation of acetate-binding MIPs include acetate salts, propionate salts, isobutyrate salts, butyrate salts, pivalate salts benzoate salts, malonate salts, succinate salts, bicarbonate salts, carbonate salts and the like. Exemplary salts include potassium salts and sodium salts.

4.2.5. Exemplary MIP Synthesis Processes

MIPs of the present disclosure can be synthesized under conditions such that its particle size, stability, and selectivity are at optimal levels, for example, for oral administration. The following MIP Synthesis Process is an exemplary process for making a MIP of the disclosure (e.g., an acetate-binding MIP). Additional MIP synthesis processes are described in Sections 5 and 6. The exemplary MIP Synthesis Process and the processes described in Sections 5 and 6 can be adapted to make different MIPs of the disclosure by substituting template molecules, functional crosslinkers, functional monomers, secondary crosslinkers, etc.

MIP Synthesis Process

A mixture (e.g., at 60° C. to 80° C.) comprising one or more solvents (e.g., MeOH), one or more template molecules (e.g., as described in Section 4.2.4), and one of the following (i) though (iv) is degassed by bubbling an inert gas (e.g., argon or nitrogen) for a period of time (e.g., approximately 15 minutes).
  (i) one or more functional monomers and one or more secondary crosslinkers (e.g., one or more functional monomers and/or one or more secondary crosslinkers as described in Sections 4.2.1 and 4.2.2);
  (ii) one or more functional crosslinkers and one or more secondary crosslinkers (e.g., one or more functional crosslinkers and/or one or more secondary crosslinkers as described in Sections 4.2.1 and 4.2.2);
  (iii) one or more functional monomers and one or more functional crosslinkers (e.g., one or more functional monomers and/or one or more functional crosslinkers as described in Sections 4.2.1 and 4.2.2);
  (iv) one or more functional monomers, one or more functional crosslinkers, and one or more secondary crosslinkers (e.g., one or more functional monomers and/or one or more functional crosslinkers and/or secondary crosslinkers as described in Sections 4.2.1 and 4.2.2).

Thereafter, a polymerization initiator (e.g., a solution of a radical initiator, e.g., as described in Section 4.2.3) in an amount of methanol or other solvent(s)) is combined with the mixture to initiate polymerization. The mixture is kept at an appropriate temperature (e.g., 60° C.) for a period of time to allow polymerization to take place (e.g., approximately 16 hours).

One or more of following steps can optionally be performed after polymerization:
  Crushing and/or grinding the MIP into a powder (e.g., after cooling the polymerization mixture to room temperature). Crushing and/or grinding can be performed, for example, with a mill such as a roller mill, or ball mill.
  Selecting particles of a desired size, for example by filtering the powder (e.g., through one or more sieves, for example as described in Section 4.2). In some embodiments, filtering comprises passing the powder through one or more sieves, for example, one or more of a 300-mesh sieve, a 500-mesh sieve, a 900-mesh sieve, and an 1800-mesh sieve.
  Washing the MIP (e.g., with a solvent) to remove template and/or unreacted reagents. Washing can be performed, for example, by performing a wash with hot methanol and Soxhlet extraction with different solvents. The extracts from the Soxhlet extraction can be tested to confirm that no template is detected
  Drying the MIP in one or more steps, (e.g., in oven at 100° C., for example, for approximately 15 hours and/or drying under vacuum, e.g., at 60° C., for example for 2 days).

4.3. Acetate-Binding MIPs

In one aspect, the disclosure provides acetate-binding MIPs. Acetate-binding MIPs of the disclosure can, for example, one or more functional molecules as described in Section 4.2. Exemplary acetate-binding MIPs are described in this Section 4.3 and Sections 5 and 6.

In some embodiments, an acetate-binding MIP comprises or consists essentially of N,N'-methylenebis(acrylamide) (MBA) and ethylene glycol dimethacrylate (EGDA). In some embodiments, the MBA and EGDA together represent at least 80% of the dry weight of the MIP (e.g., at least 85%, at least 90%, at least 95%, at least 96%, at least 97%, at least 98%, at least 99%, or 100%), with the balance (if any) being one or more additional components such as one or more monomers, other crosslinkers and/or residual template molecules. The ratio of MBA to EGDA can range, for example, from 1:5 to 5:1 (e.g., 1:5 to 1:1 or 1:1 to 5:1). For example, the ratio can be 1:5, 1:4, 1:3, 1:2, 1:1, 2:1, 3:1, 4:1, 5:1, 2:5, 3:5, 4:5, 6:5 or any range bounded by any two of the foregoing ratios. In some embodiments, the ratio is 1:1. In some specific embodiments, the ratio is 1:1.05. As detailed in the Examples, it has been found that acetate-binding MIPs comprising MBA and EGDA have particularly advantageous properties compared to other acetate-binding MIPs.

Acetate-binding MIPs of the disclosure preferably have an acetate binding capacity in water of at least 5 mg of acetate per g of MIP (e.g., at least 10 mg of acetate per g of MIP, at least 20 mg of acetate per g of MIP, at least 30 mg of acetate per g of MIP, or at least 35 mg of acetate per g of MIP). In some embodiments, acetate-binding MIPs of the disclosure have an acetate binding capacity in water from 5 mg to 40 mg of acetate (e.g., 10 mg to 40 mg, 10 mg to 30 mg, 10 mg to 20 mg, 20 mg to 40 mg, 20 mg to 30 mg, 30 mg to 40 mg) per gram of MIP. Acetate binding capacity can be measured, for example, by ion chromatography. The following assay can be used to measure acetate binding capacity:

Incubate 10 mg of a test MIP in a sodium acetate solution (100 mM, 2 mL) for 2 hours.

After removal of the MIP from the solution by centrifugation, analyze acetate content of the remaining solution by an ion chromatography system equipped with a guard column (4×50 mm), Dionex IonPac™ AS22 analytical column (4×250 mm) and a tandem conductivity detector (Dionex, ICS-1600). An aqueous solution of 4.5 mM sodium carbonate and 1.4 mM sodium bicarbonate delivered at a flow rate of 1.0 mL/min is used as the mobile phase.

With reference to the retention time of calibrating acetate standards, identify and quantify the chromatographic peak of acetate. The concentration of acetate is quantified by an external calibration curve with a minimum of 5 calibration points.

Acetate-binding MIPs of the disclosure preferably have a higher selectivity for acetate compared to chloride, for example as reflected by the measurement of acetate-binding and chloride-binding capacities in a solution of sodium acetate and sodium chloride. The following assay can be used to compare a MIP's selectivity for acetate compared to chloride:

Incubate 10 mg of a test MIP in 2 mL of a solution of sodium acetate (10 mM) and sodium chloride (10 mM) for 2 hours.

After removal of the MIP from the solution by centrifugation, analyze acetate and chloride content of the remaining solution by an ion chromatography system equipped with a guard column (4×50 mm), Dionex IonPac™ AS22 analytical column (4×250 mm) and a tandem conductivity detector (Dionex, ICS-1600). An aqueous solution of 4.5 mM sodium carbonate and 1.4 mM sodium bicarbonate delivered at a flow rate of 1.0 mL/min is used as the mobile phase.

In some embodiments, MIPs of the disclosure have an affinity for acetate which is 10 to 100 times the affinity for chloride (e.g., 10 to 100 times, 10 to 50 times, 10 to 20 times, 25 to 100 times, 25 to 50 times, 50 to 100 times, or 50 to 75 times the affinity for acetate compared to chloride).

It has been discovered that acetate-binding MIPs made from N,N'-methylenebis(acrylamide) (MBA) and ethylene glycol dimethacrylate (EGDA) exhibit surprisingly high acetate-binding capacity, and exhibit high selectivity for acetate.

4.4. Preparations and Pharmaceutical Compositions

The disclosure provides preparations comprising a population of MIP particles as described herein. Such preparations can have high purity, for example such populations can be at least 85% pure, at least 90% pure, at least 95% pure, at least 96% pure, at least 97% pure, at least 98% pure, at least 99% pure or more than 99% pure (e.g., 99.5% pure or 99.8% pure), or any range bounded by the foregoing values, for example 85% to 95% pure 90% to 95% pure, 95% to 99% pure 97% to 99.5% pure or 98% to 99.8% pure. Purity can be measured, for example, by IR spectroscopy.

Preparations of the disclosure preferably comprise particles of a sufficiently large size so that the particles are not absorbed from the GI tract when administered orally (e.g., the particles in some embodiments have a diameter of at least 10 µm), and small enough so as to have a high target molecule capacity (e.g., the particles in some embodiments have a diameter of less than 100 µm or less than 50 µm). In some embodiments, MIP preparations of the disclosure have a D (v, 0.5) particle size from 10 µm to 50 µm (e.g., 10 µm to 40 µm, 10 µm to 30 µm, 10 µm to 20 µm, 15 µm to 50 µm, 15 µm to 40 µm, 15 µm to 30 µm, 15 µm to 25 µm, 15 µm to 20 µm, 20 µm to 50 µm, 20 µm to 40 µm, 20 µm to 30 µm, 30 µm to 50 µm, 30 µm to 40 µm, 40 µm to 50 µm, or any range bounded by any two of the foregoing values). In some embodiments, the MIP preparations of the disclosure have a D (v, 0.5) particle size from 15 µm to 25 µm (e.g., 15 µm, 16 µm, 17 µm, 18 µm, 19 µm, 20 µm, 21 µm, 22 µm, 23 µm, 24 µm, or 25 µm). In other embodiments, the MIP preparations of the disclosure have a D (v, 0.5) particle size from 10 µm to 15 µm (e.g., 10 µm, 11 µm, 12 µm, 13 µm, 14 µm, or 15 µm). D (v, 0.5) is defined as the volume median diameter. D (v, 0.5) particle size can be measured by a laser particle size analyzer, for example a BT-9300S laser particle size analyzer (Bettersize, China).

A population of MIP particles can be selected for size, for example, by filtering the MIP through one or more sieves. For example, filtering through a 300-mesh sieve can be used to provide (or remove) MIP particles less than 50 µm; filtering through a 500-mesh sieve can be used to provide (or remove) MIP particles less than 30 µm; filtering through a 900-mesh sieve can be used to provide (or remove) MIP particles less than 20 µm; filtering through a 1800-mesh sieve can be used to provide (or remove) MIP particles less than 10 µm.

The disclosure also provides pharmaceutical compositions comprising a MIP of the disclosure, e.g., an acetate-binding MIP of the disclosure, and pharmaceutical compositions comprising a preparation of the disclosure. Pharmaceutical compositions of the disclosure can be formulated for oral administration. A pharmaceutical composition of the disclosure can be, for example, a liquid (e.g., suspension or solution) or a solid dosage form (e.g. a capsule or tablet). The pharmaceutical compositions can include one or more pharmaceutically acceptable excipients.

Liquid dosage forms for oral administration include suspensions and solutions, for example, in the form of a syrup, oral drops, microemulsion, or nanosuspension. Liquid dosage forms can comprise the MIP and one or more liquid excipients, for example, water, saline, ethanol, propylene glycol, 1,3-butyleneglycol, an oil (e.g., cottonseed oil, groundnut oil, corn germ oil, olive oil, castor oil, sesame oil, and mixtures thereof), glycerol, a polyethylene glycol, and combinations thereof.

Solid dosage forms for oral administration include capsules, tablets (e.g.; orally disintegrating tablets, chewable tablets, dispersible tablets, effervescent tablets, etc.), powders, granules, oral strips, chewing gums, and troches. In such solid dosage forms, a MIP can be admixed with one or more excipients for example, one or more starches, lactose, dextrose, sucrose, glucose, mannitol, silicic add, carboxymethylcellulose, an alginate, gelatin, polyvinylpyrrolidone, sucrose, acacia, agar-agar, calcium carbonate, talc, calcium stearate, magnesium stearate, a solid polyethylene glycol, sodium lauryl sulfate, or mixtures thereof, Capsule dosage forms can include a hard or soft shell, for example comprising gelatin, hypromellose, or pullulan. Solid dosage forms, such as dispersible tablets, effervescent tablets, powders, and granules, can be dissolved or dispersed in a liquid or added to food prior to administration.

4.5. Therapeutic Uses

MIPs of the disclosure can be used in the manufacture of medicaments, for example, pharmaceutical compositions for use in methods of sequestering target molecules in the gastrointestinal (GI) tract of a subject, for example as described in Section 6.

The MIPs, preparations, and pharmaceutical compositions of the disclosure can be used to sequester target molecules, e.g., microbiota derived metabolite such as acetate or other target molecule described herein, in the GI tract of a subject (e.g., a human subject). For example, acetate-binding MIPs of the disclosure can be used to treat a subject diagnosed with or at risk of a condition associated with accumulation of acetate, for example metabolic syndrome and/or obesity. In some embodiments, an acetate-binding MIP of the disclosure can be administered to a subject to reduce the body weight of the subject.

The MIPs, preparations, and pharmaceutical compositions can be administered orally. For example, a MIP, preparation, or pharmaceutical composition can be mixed with a liquid (e.g., water) or mixed with food prior to administration.

MIPs, preparations, and pharmaceutical compositions of the disclosure can, in some embodiments, be administered daily, for example once per day or multiple times per day (e.g., with each meal). The amount of MIP administered per day can range, for example, from 100 mg to 500 g per day (e.g., 100 mg to 1 g, 1 g to 5 g, 1 g to 10 g, 5 g to 15 g, 10 g to 25 g, 20 g to 50 g, 20 g to 100 g, 50 g to 100 g, 50 g to 200 g, 100 g to 200 g, 100 g to 500 g, 200 g to 500 g, or 300 g to 500 g).

5. EXAMPLES

5.1. Example 1: Acetate-Binding MIP

5.1.1. Synthesis and Characterization

A mixture of acrylamide (15.8 g, 0.222 mol) (monomer), N,N-methylene bis(acrylamide) (42.0 g, 0.273 mol) (crosslinker), sodium benzoate (5.0 g, 0.034 mol) (template molecule) in DMSO (150 mL) was heated to 70° C. and degassed by bubbling argon for 15 mins. Subsequently, 2,2'-azobisisobutyronitrile (50 mg, 0.3 mmol) as radical initiator was added to the mixture. The resulting mixture was maintained at 70° C. for 16 hours, during which a MIP was formed.

The MIP was crushed and washed with hot methanol and water. It was further ground and passed through a sieve to afford MIP particles with a particle size <50 µm. The MIP was washed with methanol, water and acetone by Soxhlet extraction until no reactant residues were detected by IR spectroscopy. The MIP was vacuum dried at 70° C. for five days prior to use in an in vivo study. IR (KBr disc, v/cm$^{-1}$): 2940 (m), 2866 (m), 1660 (vs), 1529 (vs), 1450 (m), 1417 (w), 1385 (m), 1340 (w), 1290 (m), 1217 (m), 1112 (m), 985 (w). Acetate binding affinity: 10.2 mg/g in water.

5.1.2. In Vivo Activity Study

A diet-induced obesity mouse model was used to investigate the in vivo effects of the acetate-binding MIP. C57BL/6 mice were fed with a custom high-fat diet (HFD) (Envigo, TD.06414) with or without the acetate-binding MIP. The HFD had 5.1 kcal/g with a composition of 23.5% protein, 27.3% carbohydrate and 34.3% fat. About 60% of the total calories came from fat. A total of 24 C57BL/6 mice at 15-17 weeks of age were fed with HFD ad libitum for 5 weeks prior to the start of the study. After the 5-week period, the mice were randomly divided into three groups. Mice in group A (n=9) were put on HFD mixed with the acetate-binding MIP at 15% of total food weight. Mice in group B (n=9) were put on HFD mixed with polypropylene powder (averaged particle size of about 40 µm) as a control polymer at 15% of total food weight. Mice in group C (n=6) were continued on the HFD.

Figure 1:
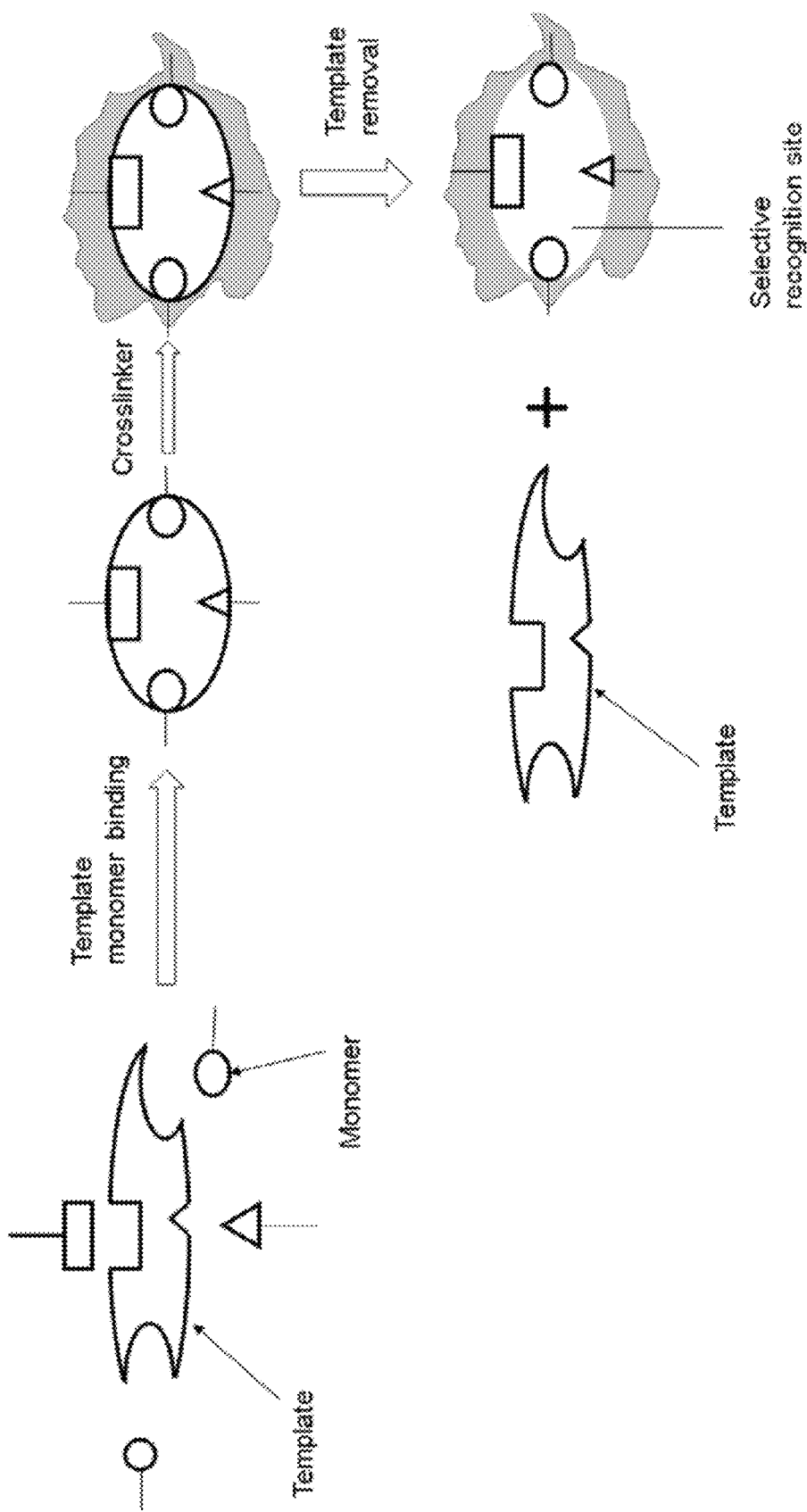
FIG. 1 is an exemplary schematic diagram showing the synthesis of a MIP.
Figure 2:
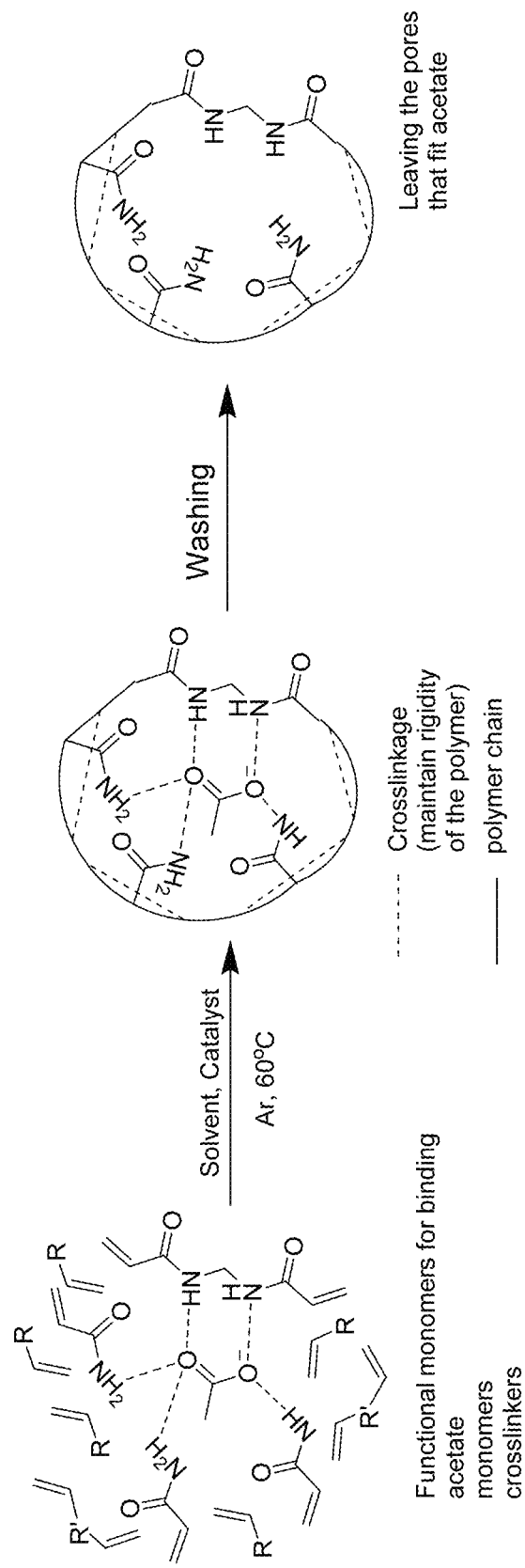
FIG. 2 is an exemplary schematic diagram showing the synthesis of an exemplary acetate-binding MIP.
Figure 3:
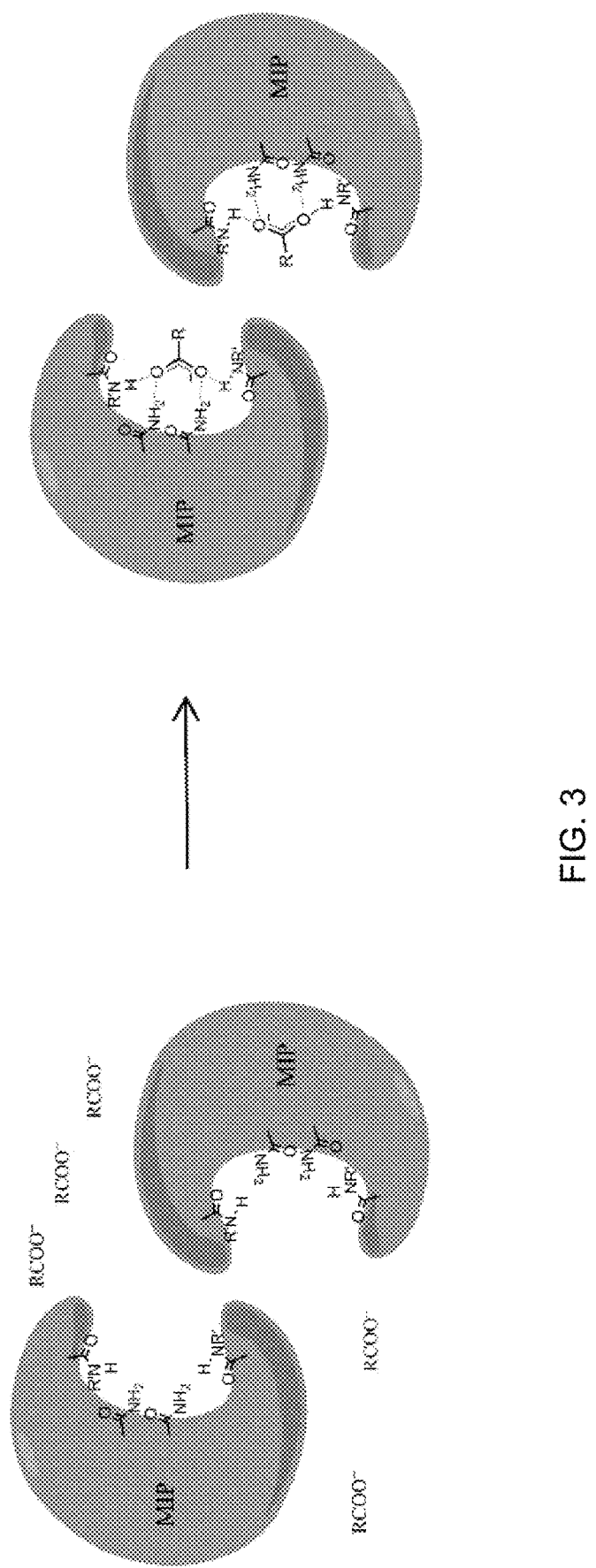
FIG. 3 is an exemplary illustration of an acetate-binding MIP binding to and sequestering an acetate target molecule.
Figure 4:
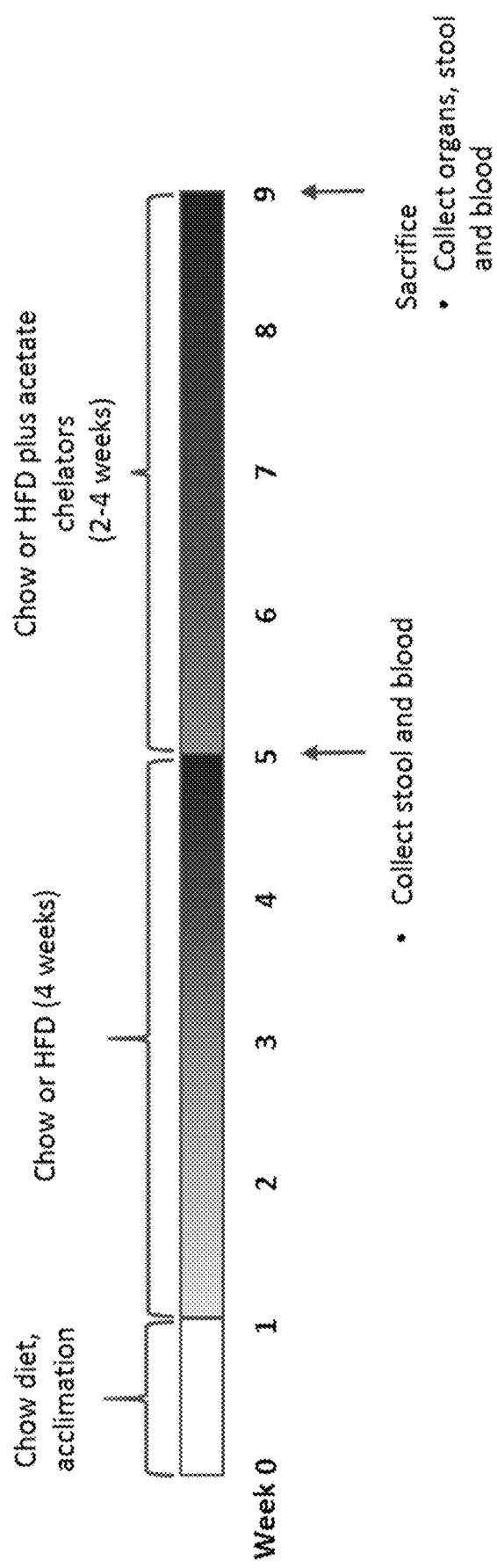
FIG. 4 is a schematic diagram showing the timeline of the study described in Example 1.

Body weight and food intake were measured five times per week. All mice were sacrificed at study end and their organs, stool and blood were collected for evaluation the toxicity and physiological effects. The experimental timeline is shown in FIG. 4. Total cholesterol levels and toxicity based on liver function, renal function and reverse-transcriptase polymerase chain reaction (RT-PCR) of immune genes from the expression of TNF-alpha, IL-la, IL-6 were analyzed.

5.1.3. Results

All mice gained weight steadily and in a similar manner during the 5 weeks of HFD prior to the study period. The average weight gain was 7.77±1.79 grams for animals in Group A, 7.80±1.52 grams for animals in Group B, and 6.75±1.49 grams for animals in Group C (p=0.362). After 4 weeks of the study period, mice in Group A fed with HFD mixed with acetate-binding MIPs lost weight compared to those fed with HFD with control polymer (polypropylene) or no polymer. The average weights of the animals are shown in FIG. 5A. Overall, the mice in Group A lost 0.88±1.27 grams of weight, compared with weight gain of 2.90±1.13 grams in Group B and 2.11±0.34 grams in Group C (FIG. 5B). The Kruskal-Wallis test of weight change was significant between groups (p=0.0004), as was the Mann-Whitney U tests showing significant weight loss in Group A compared with Group B (adjusted p=0.0003) and with Group C (adjusted p=0.025). There was no significant weight change between the two control groups (Groups B and C, adjusted p=1.000). Taking the weights of the polymers into account, the net food weight consumed by mice in the three groups were similar (Group A: 2.56±0.42 grams/mouse/day, Group B: 2.44±0.31 grams/mouse/day, Group C: 2.54±0.26 grams/ mouse/day, p=0.477).

Total cholesterol was lower in Group A compared to Group B and Group C (FIG. 5C)

No significant differences in liver function, renal function and expression of TNF-alpha, IL-la, IL-6 between groups were observed (FIG. 5D-FIG. 5F).

5.2. Example 2: Second Generation Acetate-Binding MIPs

5.2.1. Materials and Methods

5.2.1.1. Materials and Reagents

Acrylamide, ethylene glycol dimethacrylate (EGDA), divinylbenzene (DVB), pentaerythritol triacrylate (PETA), trimethylolpropane trimethacrylate (TMPTMA), acryloyloxyethyltrimethyl ammonium chloride (NAAC), N,N-methylenebis(acrylamide) (MBA), sodium persulfate, ammonium persulfate, and potassium acetate were purchased from J&K Chemicals Ltd. N-Isopropylacrylamide (NIPA) and N-ethylacrylamide (NEA) were obtained from Acros Organics Chemical Company. Sodium acetate was purchased from Riedel-de Haën. Sodium chloride, sodium hydrogen carbonate, and sodium chloride were obtained from Uni-Chem Inc. All solvents including acetone, dimethyl sulfoxide, dimethylformamide, tetrahydrofuran, methanol and ethanol were of analytical reagent grade and were used without further purification. Milli-Q water was prepared by using Millipore Milli-Q gradient A10 system.

5.2.1.2. General MIP Synthetic Route (Small Scale)

To a 20-mL tube containing 3 mL solvent such as THF, DMF and/or MeOH was added a mixture of functional monomer/crosslinker, crosslinker and template in the ratio of 4:10:1 (FIG. 6). The resulting mixture was degassed by bubbling argon for 15 mins and heated to 60° C. Thereafter, a solution of radical initiator in 0.5 ml of solvent was added to the reaction mixture in a dropwise manner to initiate polymerization. The reaction mixture was kept at 60° C. for an additional 16 hours. After cooling to room temperature, the resulting MIP was crushed into small pieces and finely ground into a powder. After washing with hot methanol, the powder was further washed with Soxhlet extraction with methanol (3 days), milli-Q water (3 days) and acetone (1 day). The extracts from the Soxhlet extraction were tested to confirm no reagent residues could be detected. The powder was then dried overnight in an oven at 80° C. Further drying was achieved by vacuum drying at 60° C. for 2 days.

5.2.1.3. Synthesis of P1-P9

In initial studies, it was found that polymers crosslinked by DVB, PETA, TMPTMA, showed very low acetate-binding affinity. Without being bound by theory, it is believed that the weak binding affinity was likely due to the weak binding of these crosslinkers for the counter cations, and believed that the acetate-binding would also be significantly reduced. For the polymers with NAAC, the reaction yielded a gel instead of polymer. Following the initial studies, polymers (P1-P9) based on different combinations of acrylamide, MBA and EGDA were further investigated. Their synthetic routes are summarized in FIGS. 7A-7B. Table 1 summarizes the starting materials used to synthesize P1-P9.

5.2.1.3.1. Detailed Synthetic Procedure for P6

To a 20-mL tube containing 3 mL MeOH, a mixture of 0.46 g acrylamide (functional monomer), 2.5 g N,N'-methylene bis(acrylamide) (MBA) (functional crosslinker) and 0.134 g sodium acetate was added. The resulting mixture was degassed with argon for 15 min and heated to 70° C. At this temperature, a suspension of 40 mg ammonium persulfate in 0.5 ml of MeOH was added in a dropwise manner to initiate the polymerization. The reaction mixture was kept at 70° C. for and additional 16 hours. The resulting polymer was crushed, washed with hot methanol and finely ground into a powder. To exclude polymer size >40 μm, the MIP was filtered through a 300-mesh sieve. The powder was washed with methanol (5 days), milli-Q water (5 days) and EtOH (2 days) using Soxhlet extraction. After washing, the powder was dried overnight at 80° C. in an oven and further vacuum dried at 60° C. for 2 days.

5.2.1.3.2. Detailed Synthetic Procedure for P8

To a 20-mL tube containing 3 mL MeOH, a mixture of 0.46 g acrylamide (functional monomer), 2.7 g EGDA (secondary crosslinker) and 0.132 g sodium acetate as template was added. The resulting mixture was degassed with argon for 15 min and heated to 80° C. A solution of 20 mg ammonium persulfate in 0.5 ml of MeOH was then added in a dropwise manner to initiate the polymerization. Thereafter, the reaction mixture was kept at 80° C. for additional 16 hours. The resulting polymer was crushed, washed with hot methanol and finely ground into a powder. To exclude polymer size >40 μm, the MIP was filtered through a 300-mesh sieve. The powder was further washed with methanol (3 days), millii-Q water (3 days) and acetone (1 day) using Soxhlet extraction. After washing, the powder was dried overnight at 80° C. in an oven and further vacuum dried at 60° C. for 2 days.

5.2.1.3.3. Detailed Synthetic Procedure for $P9_3$

To a 20-mL tube containing 3 mL MeOH, a mixture of 2 g (MBA) (functional crosslinker), 2.7 g EGDA (secondary crosslinker) and 0.4 g potassium acetate as template was added. The resulting mixture was degassed with argon for 15 min and then heated to 70° C. At this temperature, a suspension of 40 mg ammonium persulfate in 0.5 ml of MeOH was added in a dropwise manner to initiate the polymerization. The reaction mixture was kept at 70° C. for

TABLE 1

| | Mole Ratio | | | | | | | |
| | Monomers | | | Crosslinkers | | Template Molecules | | |
| MIP | Acrylamide | NIPA | NEA | MBA | EGDA | NaOAc | KOAc | $C_6H_5COONa$ |
| --- | --- | --- | --- | --- | --- | --- | --- | --- |
| P1 | 2 | | | | 10 | 1 | | |
| P2 | 4 | | | | 10 | | 1 | |
| P3 | 4 | | | | 10 | | | 1 |
| P4 | 6 | | | | 10 | 1 | | |
| P5 | | 4 | | | 10 | 1 | | |
| P6 | 4 | | | 10 | | 1 | | |
| P7 | | | 4 | | 10 | 1 | | |
| P8 | 4 | | | | 10 | 1 | | |
| $P9_1$ | | | | 2 | 5 | 1 | | |
| $P9_2$ | | | | 1 | 5 | 1 | | |
| $P9_3$ | | | | 4 | 4.2 | 1 | | |
| $P9_4$ | | | | 6 | 5 | 1 | | | an additional 16 hours. The resulting polymer was crushed, washed with hot methanol and finely ground into a powder. To exclude polymer size >40 μm, the MIP was filtered through a 300-mesh sieve. The powder was washed with methanol (5 days), milli-Q water (5 days) and EtOH (2 days) using Soxhlet extraction. After washing, the powder was dried overnight at 80° C. in an oven and further vacuum dried at 60° C. for 2 days.

5.2.1.4. Detailed Synthetic Procedure for $P9_3$ in Large Scale (P90

In a 500-mL round bottom flask containing 60 ml MeOH, a mixture of 40 g MBA (functional crosslinker), 54 g EGDA (secondary crosslinker) and 8 g potassium acetate. The resulting mixture was degassed with argon for 15 min and then heated to 70° C. At this temperature, a suspension of 400 mg ammonium persulfate in 5 ml of MeOH was slowly added to initiate the polymerization. The reaction mixture was kept at 70° C. for additional 16 hours. The resulting polymer was crushed, washed with hot methanol, and finely ground into a powder with a grinder. The powder was passed through a 300-mesh sieve to to exclude polymer size >40 μm. The powder was washed with methanol (5 days), milli-Q water (5 days) and EtOH (2 days) using Soxhlet extraction. After washing, the powder was dried in oven at 80° C. for 15 hours and then further dried under vacuum at 60° C. for 2 days.

5.2.1.5. Physical Measurements and Instrumentation

Infrared (IR) spectra were obtained on KBr discs by using a Perkin-Elmer Spectrum 100 FTIR spectrophotometer. The thermogravimetric analysis (TGA) was carried out on a PerkinElmer STA6000. 5-10 mg of samples in a holder with nitrogen atmosphere were used for TGA measurements, which were conducted from 30° C. to 700° C. with a heating rate of 5° C./min.

5.2.1.6. Acetate Binding Affinity Studies

Binding affinity studies were carried out by incubating 10 mg of a MIP in a sodium acetate solution (100 mM, 2 mL) for 2 hours. After removal of the MIP from the solution by centrifugation, the acetate content was analyzed by Ion Chromatography equipped with guard column (4×50 mm), Dionex IonPac™ AS22 analytical column (4×250 mm) and a tandem conductivity detector (Dionex, ICS-1600). An aqueous solution of 4.5 mM sodium carbonate and 1.4 mM sodium bicarbonate delivered at a flow rate of 1.0 mL/min was used as the mobile phase. With reference to the retention time of calibrating acetate standards, chromatographic peak of acetate was identified and quantified. The concentration of acetate was quantified by an external calibration curve with a minimum of 5 calibration points.

5.2.1.7. In Vivo Study

An in vivo study was performed similar to Example 1. In this study, obesity was induced in mice (n=5 per group) with HFD for four weeks. After the four-week weight gain period, MIP $P9_L$ was mixed in their diet at increasing amount of 0%, 1%, 5%, 15% and 25% by volume. The weight, daily water consumption, and daily food consumption were measured. The general condition and well-being of the mice were monitored. The results of the in vivo study are shown in FIG. 9 (for MIP $P9_L$) and FIG. 11 (for MIP P8).

5.2.1.8. Mutagenicity Assay $P9_L$ was evaluated its potential to induce point mutations in *Salmonella typhimurium* strains TA98, TA100, TA1535, TA1537, and *Escherichia coli* strain WP2 uvrA. The experimental design followed the OECD Guideline for Testing of Chemicals—471, Bacterial Reverse Mutation Test (Ames assay).

5.2.2. Results and Discussion

5.2.2.1. Yield, IR Spectra, Thermal Stability

Yield and infrared spectral absorption data for P1-P9 are shown in Table 2.

TABLE 2

| MIP | Yield[a] (%) | Infrared absorption (v/cm$^{-1}$) |
|---|---|---|
| P1 | 62 | 955(w), 1052(w), 1164(vs), 1264(m), 1388(w), 1457(m), 1642(w), 1671(w), 1727(vs), 2899(w), 2956(m), 2998(m), 3459 br (s) |
| P2 | 64 | 954(w), 1051(w), 1163(vs), 1262(m), 1389(w), 1459(m), 1639(w), 1673(m), 1728(vs), 2895(w), 2958(m), 2999(m), 3464 br (s) |
| P3 | 68 | 960(w), 1055(w), 1162(vs), 1266(m), 1390(w), 1459(m), 1643(w), 1672(m), 1729(vs), 2851(w), 2955(m), 2990(m), 3455 br(s) |
| P4 | 65 | 964(w), 1056(w), 1157(vs), 1264(m), 1388(w), 1458(m), 1644(w), 1670(m), 1730(vs), 2847(w), 2953(m), 2994(m), 3458 br (s) |
| P5 | [b] | 962(w), 1159(vs), 1266(m), 1389(w), 1456(m), 1673(m), 1728(vs), 2852(m), 2956(m), 2994(m), 3450 br (s) |
| P6 | 64 | 985 (w), 1112 (m), 1217 (m), 1290 (m), 1340 (w), 1385 (m), 1419 (w), 1449 (m), 1529 (vs), 1660 (vs), 2866 (m), 2940 (m), 3448 br (s) |
| P7 | [b] | 965(w), 1165(vs), 1268(m), 1395(w), 1454(m), 1672(m), 1731(vs), 2852(m), 2953(m), 2994(m) , 3434 br (s) |
| P8 | 52[c] | 954(w), 1051(w), 1163(vs), 1262(m), 1389(w), 1459(m), 1639(w), 1673(m), 1728(vs), 2895(w), 2958(m), 2999(m), 3464 br (s) |
| $P9_1$ | 62[c] | 1154(s), 1249(m), 1384(m), 1462(w), 1523(m), 1655(m), 1725(s), 2853(w), 2918(w), 2955(m), 2991(w), 3448 br(s) |
| $P9_2$ | 68[c] | 1144(s), 1242(s), 1384(w), 1458(w), 1528(m), 1663(m), 1725(s), 2851(w), 2922(w), 2957(m), 2986(m), 3431 br(s) |
| $P9_3$ | 59[c] | 1154(s), 1248(m), 1384(m), 1462(w), 1523(m), 1655(s), 1725(s), 2853(w), 2918(w), 2955(m), 2991(w), 3448 br(s) |

TABLE 2-continued

| MIP | Yield[a] (%) | Infrared absorption (v/cm$^{-1}$) |
|---|---|---|
| P9$_4$ | 60[c] | 1147(s), 1240(m), 1389(w), 1459(w), 1532(s), 1669(s), 1726(s), 2847(w), 2957(m), 2986(w), 3433 br (vs) |
| P9$_L$ | | 1156(s), 1246(m), 1384(m), 1460(w), 1526(m), 1658(s), 1725(s), 2852(w), 2920(w), 2956(m), 2991(w), 3436 br(s). |

Yields = (dried weight of MIP/total weight of monomers and crosslinkers).
[b]Yield could not be obtained due to the formation of gel-like polymers.
[c]Yield of MIP with particle size < 40 μm.

The thermal stability of P6, P8 and P9$_L$ were examined by TGA. As shown in the TGA thermograms of FIG. 8A-FIG. 8C, all tested MIPs show high thermal stability without decomposition up to ca. 240° C., as reflected from the minimal weight lost. Increasing the temperature above 250° C., the weights of these polymers start to decrease, suggesting the decomposition of the polymer. When temperature increases to about 315 to 330° C., the rate of weight-loss increase drastically. Less than 5% of the original weight of MIPs remained when the temperature reached 475° C. This confirms the thermal stability of these polymers under physiological temperatures.

5.2.2.2. Acetate-Binding Properties

As mentioned above, polymers crosslinked by DVB, PETA and TMPTMA showed very low acetate binding affinity, which, again without being bound by theory, is attributed to the weak binding of these crosslinkers for the counter cations. The acetate-binding capacity of several MIPs were measured by ion-chromatography and the results are summarized in Table 3-Table 4. P6 prepared in Example 2 show much lower binding capacity compared to the MIP of Example 1 prepared with the same building blocks in DMSO with the use of AIBN as initiator. For MIPs prepared using MeOH as solvent and persulfate as initiator, P9$_L$ showed the highest acetate-binding capacity for acetate (Table 3). Therefore, P9$_L$ synthesized in large scale and used for the in vivo animal study to determine the dosage-response relationship.

To provide insights into the effect of solvent medium on the binding capacity, the acetate-binding capacity of P6, P8 and P9$_L$ in methanol was determined. Without being bound by theory, it is believed that the much higher binding capacity of acetate in MeOH is due to weaker solvation of acetate in MeOH. P9$_L$ with different particle sizes was prepared and their acetate-binding capacity was determined. The results (Table 4) reveal that polymers with smaller particle size show a higher binding capacity.

TABLE 3

| Polymer | Acetate-binding capacity (mg/g) in water | Acetate-binding capacity (mg/g) in methanol |
|---|---|---|
| P1 | 2.42 | |
| P2 | 12.32 | |
| P3 | 8.20 | |
| P4 | 7.82 | |
| P6 | 7.19 | 39.67 |
| P8 | 10.37 | 42.27 |
| P9$_L$ | 33.47 | 95.16 |

TABLE 4

| P9$_L$ Particle Size | Acetate-binding capacity (mg/g) in water | Acetate-binding capacity (mg/g) in methanol |
|---|---|---|
| 10 μm to 20 μm | 39.38 | 84.90 |
| 20 μm to 30 μm | 32.44 | 78.86 |
| 30 μm to 40 μm | 31.45 | 72.40 |

5.2.2.3. In Vivo Study

Results of the primary endpoint (weight) of the in vivo study for MIP P9$_L$ are shown in FIG. 9. The mice had incremental weight loss when fed diets with increasing amount of MIP. There was no significant liver toxicity (indicated by liver enzymes ALT and AST) or mucosal injury (indicated by iFABP and FIT) observed in mice administered P9$_L$.

Acetate-binding MIP P8 was also evaluated in an in vivo study. The results are shown in FIG. 11. Comparing FIG. 5A, FIG. 9, and FIG. 11, P9$_L$ appears to be more effective at reducing body weight than the MIP of Example 1 and P8.

5.2.2.4. Mutagenicity

P9$_L$ was not found to be mutagenic to *S. typhimurium* strains TA98, TA100, TA1535 and TA1537 and *E. coli* strain WP2 uvrA under the conditions of the test.

5.3. Example 3: Additional Acetate-Binding MIPs

5.3.1. MIP Synthesis

Several different acetate-binding MIPs were made according to the following general synthetic route.

A mixture comprising functional molecules, secondary crosslinkers (when used) and template molecules dissolved in a solvent at 60° C.-80° C. was degassed by bubbling argon or nitrogen for 15 minutes. Thereafter, a solution of radical initiator in a minimum amount of methanol or other solvent was added into the mixture to initiate polymerization. The reaction mixture was kept at 60° C. for additional 16 hours. After cooling to room temperature, the resulting polymer was crushed into small pieces, finely ground into a powdery form and filtered through a sieve to collect imprinted polymers of desirable particle sizes. After washing, the powder was dried in oven at 100° C. for 15 hours and then further dried under vacuum at 60° C. for 2 days. Washing of the MIP was typically performed by washing with hot methanol and then Soxhlet extraction with different solvents.

5.3.2. P-OAc-1

An acetate-binding MIP was made with the following reagents: functional crosslinker: 40 g N,N-methylenebis (acrylamide) (MBA); secondary crosslinker: 54 g ethylene glycol dimethacrylate (EGDA); template molecule: 8 g potassium acetate; solvent: 60 mL methanol; initiator: 0.3 g ammonium persulfate. Yield: 60%. IR (KBr, cm$^{-1}$): 1156(s), 1246(m), 1384(m), 1460(w), 1526(m), 1658(s), 1725(s), 2852(w), 2920(w), 2956(m), 2991(w), 3436 br(s). Acetate-binding capacity: 33.5 mg/g in water; 95.2 mg/g in methanol.

5.3.3. P-OAc-2

An acetate-binding MIP was made with the following reagents: functional monomer: 4.6 g acrylamide; secondary crosslinker: 27 g EGDA; template molecule: 1.32 g sodium acetate; solvent: 30 mL DMSO; initiator: 0.2 g AIBN. Yield: 52%. IR (KBr, cm$^{-1}$): 954(w), 1051(w), 1163(vs), 1262(m), 1389(w), 1459(m), 1639(w), 1673(m), 1728(vs), 2895(w), 2958(m), 2999(m), 3464 br (s). Acetate-binding: 10.3 mg/g in water; 42.3 mg/g in methanol.

5.3.4. P-OAc-3

An acetate-binding MIP was made with the following reagents: functional crosslinker: 5.0 g 1,3-bis(4-(allyloxy)phenyl)urea; secondary crosslinker: 13.2 g 1,2-diallyloxybenzene; secondary crosslinker: 10.9 g divinylbenzene; template molecule: 1.55 g potassium acetate; solvent: 45 mL methanol:DMF (1:1); initiator: 0.5 g 2,2'-azobis(2-methylpropionate). Yield: 55%.

5.3.5. P-OAc-4

An acetate-binding MIP was made with the following reagents: functional crosslinker: 4.1 g 1,3-bis(4-vinylphenyl)urea; secondary crosslinker: 13.2 g 1,2-diallyloxybenzene; secondary crosslinker: 10.9 g divinylbenzene; template molecule: 1.55 g potassium acetate; solvent: 45 mL methanol:DMF (1:1); initiator: 0.5 g 2,2'-azobis(2-methylpropionate). Yield: 58%.

5.3.6. P-OAc-5

An acetate-binding MIP was made with the following reagents: functional crosslinker: 5 g 1,3-diallylurea; secondary crosslinker: 6.9 g 1,2-diallyloxybenzene; secondary crosslinker: 5.6 g 1,3-diisopropenylbenzene; template molecule: 1.7 g potassium acetate; solvent: 20 mL methanol; initiator: 0.3 g 2,2'-azobis(2-methylpropionate). Yield: 64%.

5.3.7. P-OAc-6

An acetate-binding MIP was made with the following reagents: functional crosslinker: 5 g 1,3-diallylurea; secondary crosslinker: 9.4 g 1,3-diisopropenylbenzene; template molecule: 1.7 g potassium acetate; solvent: 20 mL methanol; initiator: 0.3 g 2,2'-azobis(2-methylpropionate). Yield: 73%.

5.3.8. P-OAc-7

An acetate-binding MIP was made with the following reagents: functional crosslinker: 5 g 1,3-diallylurea; secondary crosslinker: 11.3 g 1,2-diallyloxybenzene; template molecule: 1.7 g potassium acetate; solvent: 20 mL methanol; initiator: 0.3 g 2,2'-azobis(2-methylpropionate). Yield: 62%.

5.3.9. P-OAc-8

An acetate-binding MIP was made with the following reagents: functional crosslinker: 5 g 1,3-diallylurea; secondary crosslinker: 11.6 g divinylbenzene; template molecule: 1.7 g potassium acetate; solvent: 20 mL methanol; initiator: 0.2 g 2,2'-azobis(2-methylpropionate). Yield: 60%.

5.3.10. P-OAc-9

An acetate-binding MIP was made with the following reagents: functional crosslinker: 5 g 1,3-diallylurea; secondary crosslinker: 7.6 g divinylsuccinate; template molecule: 1.7 g potassium acetate; solvent: 15 mL methanol; initiator: 0.2 g 2,2'-azobis(2-methylpropionate). Yield: 65%.

5.3.11. P-OAc-10

An acetate-binding MIP was made with the following reagents: functional crosslinker: 5 g 1,3-diallylurea; secondary crosslinker: 15 g divinylsuccinate; template molecule: 1.7 g potassium acetate; solvent: 15 mL methanol; initiator: 0.2 g 2,2'-azobis(2-methylpropionate). Yield: 75%.

5.4. Example 4: Comparison of Acetate-Binding MIPs

Various acetate-binding MIPs were compared. A summary of their components, reaction conditions, and properties is shown in Table 5. Various acetate-binding MIPs having high acetate binding capacity were identified. When compared to other acetate binding MIPs, $P9_L$ was found to have superior acetate binding capacity and good selectivity for acetate over chloride.

TABLE 5

| No. | Functional Molecule ("FM") | FM Type | Crosslinker ("CL") | FM:CL Ratio | Reaction Conditions | Particle Density | Acetate binding capacity | Selectivity for Acetate | Comments |
| --- | --- | --- | --- | --- | --- | --- | --- | --- | --- |
| 1. | N-Isopropylacrylamide | M | Ethylene glycol dimethacrylate (EGDA) | 4:5-2:5 | MeOH, 80° C., persulfate | ND | ND | ND | gel-like solid |
| 2. | N-ethylamide | M | Ethylene glycol dimethacrylate (EGDA) | 4:5-2:5 | MeOH, 80° C., persulfate | ND | ND | ND | gel-like solid |
| 3. | acryloyloxyethyltrimethyl ammonium chloride | M | Ethylene glycol dimethacrylate (EGDA) | 4:5-2:5 | MeOH, 80° C., persulfate | ND | | ND | gel-like solid |
| 4. | N,N'-methylenebis(acrylamide) | CL | Divinylbenzene | 3:5 | MeOH, 80° C., persulfate | <1 g/cm3 | <0.5 mg/g | ND | float on water |
| 5. | N,N'-methylenebis(acrylamide) | CL | pentaerythritol triacrylate | 3:5 | MeOH, 80° C., persulfate | >1 g/cm3 | <0.5 mg/g | ND | |

TABLE 5-continued

| No. | Functional Molecule ("FM") | FM Type | Crosslinker ("CL") | FM:CL Ratio | Reaction Conditions | Particle Density | Acetate binding capacity | Selectivity for Acetate | Comments |
|---|---|---|---|---|---|---|---|---|---|
| 6. | N,N'-methylenebis(acrylamide) | CL | trimethylolpropane trimethacrylate | 3:5 | MeOH, 80° C., persulfate | >1 g/cm3 | <0.5 mg/g | ND | |
| 7. (P6) | N-acrylamide | M | N,N'-methylenebis(acrylamide) | 4:10 | DMSO, 100° C., AIBN | >1 g/cm3 | 7.2 mg/g | Good selectivity | |
| 8. (P8) | N-acrylamide | M | N,N'-methylenebis(acrylamide) | 4:10 | MeOH, 80° C., persulfate | >1 g/cm3 | 10.4 mg/g | Also captures chloride | |
| 9. (P9$_L$) | N,N'-methylenebis(acrylamide) | CL | Ethylene glycol dimethacrylate (EGDA) | 4:4.2 | MeOH, 80° C., persulfate | >1 g/cm3 | 33.5 mg/g | Good selectivity | |
| 10. (P1) | N-acrylamide | M | Ethylene glycol dimethacrylate (EGDA) | 2:10 | MeOH, 80° C., persulfate | >1 g/cm3 | 2.4 mg/g | ND | |
| 11. (P4) | N-acrylamide | M | Ethylene glycol dimethacrylate (EGDA) | 6:10 | MeOH, 80° C., persulfate | >1 g/cm3 | 7.8 mg/g | Also captures chloride | |
| 12. | 1-3-bis(4-(allyloxy)phenyl)urea, | CL | 1,2-diallyloxybenzene, Divinylbenzene | 1:4.5,4.5 | MeOH, DMF 80° C., V601 | >1 g/cm3 | ND | ND | |
| 13. | 1,3-bis(4-vinylphenyl)urea | CL | 1,2-diallyloxybenzene, Divinylbenzene | 1;4.5,4.5 | MeOH, DMF 80° C., V601 | >1 g/cm3 | ND | ND | |
| 14. | 1,3-diallylurea | CL | 1,2-diallyloxybenzene, 1,3-diisopropenylbenzene | 1;1,1 | MeOH, 80° C., V601 | ND | ND | ND | No rigid polymer formed |
| 15. | 1,3-diallylurea | CL | 1,2-diallyloxybenzene | 1:2 | MeOH, 80° C., V601 | ND | ND | ND | No rigid polymer formed |
| 16. | 1,3-diallylurea | CL | 1,3-diisopropenylbenzene | 2:3 | MeOH, 80° C., V601 | ND | ND | ND | No rigid polymer formed |
| 17. | 1,3-bis(4-(allyloxy)phenyl)urea | CL | Di(ethylene glycol) divinyl ether | 4:5 | MeOH, DMF 80° C., V601 | ND | ND | ND | gel-like solid |
| 18. | 1,3-bis(4-vinylphenyl)urea | CL | Di(ethylene glycol) divinyl ether | 4:5 | MeOH, DMF 80° C., V601 | ND | ND | ND | gel-like solid |
| 19. | 1,3-bis(4-(allyloxy)phenyl)urea | CL | tri(ethylene glycol) divinyl ether | 4:5 | MeOH, DMF 80° C., V601 | ND | ND | ND | gel-like solid |
| 20. | 1,3-bis(4-vinylphenyl)urea | CL | tri(ethylene glycol) divinyl ether | 4:5 | MeOH, DMF 80° C., V601 | ND | ND | ND | gel-like solid |
| 21. | 1,3-bis(4-vinylphenyl)urea | CL | 1,3-divinyltetramethyldisiloxane | 4:5 | MeOH, DMF 80° C., V601 | ND | ND | ND | No polymer formed |
| 22. | 1,3-diallylurea | CL | Divinylbenzene | 2:5 | MeOH, 70° C., V601 | >1 g/cm3 | ND | ND | |
| 23. | 1,3-diallylurea | CL | Divinylsuccinate | 2:5-4:5 | MeOH, 70° C., V601 | >1 g/cm3 | ND | ND | |

M = monomer;
CL = crosslinker;
ND = Not Determined

6. SPECIFIC EMBODIMENTS

The present disclosure is exemplified by the specific embodiments below.

1. A molecularly imprinted polymer (MIP) capable of binding acetate.
2. The MIP of embodiment 1, which is capable of binding acetate in a mammalian gastrointestinal tract.
3. The MIP of embodiment 1, which is capable of binding acetate in a human gastrointestinal tract.
4. The MIP of embodiment 2 or embodiment 3, wherein the acetate is produced by gut microbiota.
5. The MIP of any one of embodiments 1 to 4, which comprises one or more functional molecules, wherein each functional molecule is independently a functional crosslinker or a functional monomer.

6. The MIP of embodiment 5, wherein the one or more functional molecules have been polymerized and crosslinked.
7. The MIP of embodiment 5 or embodiment 6, wherein the one or more functional molecules comprise one or more functional crosslinkers.
8. The MIP of embodiment 7, wherein the one or more functional crosslinkers comprise one or more amide-containing crosslinkers.
9. The MIP of embodiment 8, wherein the one or more functional crosslinkers comprise or consist of N,N'-methylenebis(acrylamide) (MBA).
10. The MIP of any one of embodiments 7 to 9, wherein the one or more functional crosslinkers comprise one or more urea-containing crosslinkers.
11. The MIP of embodiment 10, wherein the one or more functional crosslinkers comprise or consist of 1,3-bis(4-vinylphenyl)urea, 1,3-bis(4-(allyloxy)phenyl)urea, 1,3-diallylurea, or a combination thereof.
12. The MIP of any one of embodiments 5 to 11, wherein the functional molecules do not comprise any functional monomers.
13. The MIP of any one of embodiments 5 to 11, wherein the functional molecules comprise one or more functional monomers.
14. The MIP of embodiment 13, wherein the one or more functional monomers comprise one or more acrylamides.
15. The MIP of embodiment 14, wherein the one or more acrylamides comprise acrylamide, an N-alkylacrylamide, a methacrylamide, or a combination thereof.
16. The MIP of embodiment 14 or embodiment 15, wherein the one or more acrylamides comprise or consist of acrylamide.
17. The MIP of embodiment 15 or embodiment 16, wherein the one or more acrylamides comprise or consist of N-methylacrylamide, N-ethylacrylamide, N-isopropylacrylamide, N-methylmethacrylamide, N-(3-aminopropyl)methacrylamide, N-(2-oxoethyl)-2-acrylamide, N-(2-aminopyridine)methacrylamide, or a combination thereof.
18. The MIP of any one of embodiments 13 to 17, wherein the one or more monomers comprise or consist of N-vinylacetamide, N-[[[3-(ethenylsulfonyl)-1-oxopropyl]amino]methyl]-2-propenamide, 4-vinylbenzamide, N-alkyl-(4-vinylbenzamide), N,N'-diethyl(4-vinylphenyl)amidine, a hydroxyl-substituted styrene, an amide-substituted styrene, N-(diaminoethylene)-2-methylprop-2-enamide, N-allylurea, 1-allyl-2-thiourea, or a combination thereof.
19. The MIP of any one of embodiments 5 to 18, which comprises the one or more functional molecules and one or more crosslinkers that are different from any functional crosslinkers (such one or more crosslinkers referred to as "secondary crosslinkers").
20. The MIP of embodiment 19, wherein the one or more secondary crosslinkers comprise or consist of ethylene glycol dimethacrylate (EGDA), ethylene glycol diacrylate, 1,2-diallyloxybenzene, divinylbenzene, 1,3-diisopropenylbenzene, divinylsuccinate, 1,3-divinyltetramethyldisiloxane, tri(ethylene glycol) divinyl ether, di(ethylene glycol) divinyl ether, trimethylolpropane trimethacrylate, pentaerythritol triacrylate, or a combination thereof.
21. The MIP of embodiment 20, wherein the one or more secondary crosslinkers comprise or consist of EGDA.
22. The MIP of any one of embodiments 19 to 21, wherein the molar ratio of the functional molecules to secondary crosslinkers is 1:5 to 5:1.
23. The MIP of embodiment 21, wherein the molar ratio of the functional molecules to secondary crosslinkers is 1:5 to 1:1.
24. The MIP of embodiment 21, wherein the molar ratio of the functional molecules to secondary crosslinkers is 1:1 to 5:1.
25. The MIP of embodiment 21, wherein the molar ratio of the functional molecules to secondary crosslinkers is 1:1 to 4:5.
26. The MIP of embodiment 25, wherein the molar ratio of the functional molecules to secondary crosslinkers is 1:1.05.
27. The MIP of any one of embodiments 5 to 18, except when depending from embodiment 12, which comprises functional monomers and functional crosslinkers and no secondary crosslinkers.
28. The MIP of embodiment 27, wherein the molar ratio of the functional monomers to the functional crosslinkers is 1:5 to 5:1.
29. The MIP of embodiment 28, wherein the molar ratio of the functional monomers to functional crosslinkers is 1:5 to 1:1.
30. The MIP of embodiment 28, wherein the molar ratio of the functional monomers to functional crosslinkers is 1:1 to 5:1.
31. The MIP of embodiment 1, which comprises N,N'-methylenebis(acrylamide) (MBA) and ethylene glycol dimethacrylate (EGDA).
32. The MIP of embodiment 31, wherein the molar ratio of N,N'-methylenebis(acrylamide) (MBA) to EGDA is 1:5 to 5:1.
33. The MIP of embodiment 32, wherein the molar ratio of N,N'-methylenebis(acrylamide) (MBA) to EGDA is 1:1 to 4:5.
34. The MIP of embodiment 33, wherein the molar ratio of N,N'-methylenebis(acrylamide) (MBA) to EGDA is 1:1.05.
35. The MIP of embodiment 1, which has IR peaks corresponding to the IR peaks of any one of the MIPs as shown in Table 2.
36. The MIP of any one of embodiments 1 to 35, wherein the MIP in water has an acetate binding capacity of at least 5 mg of acetate per g of MIP.
37. The MIP of embodiment 36, wherein the MIP in water has an acetate binding capacity from 5 mg of acetate per g of MIP to 40 mg of acetate per g of MIP.
38. The MIP of embodiment 36 or embodiment 37, wherein the MIP in water has an acetate binding capacity of at least 10 mg of acetate per g of MIP.
39. The MIP of embodiment 36 or embodiment 37, wherein the MIP in water has an acetate binding capacity of at least 20 mg of acetate per g of MIP.
40. The MIP of embodiment 36 or embodiment 37, wherein the MIP in water has an acetate binding capacity of at least 30 mg of acetate per g of MIP.
41. The MIP of embodiment 36 or embodiment 37, wherein the MIP in water has an acetate binding capacity of at least 35 mg of acetate per g of MIP.
42. The MIP of any one of embodiments 36 to 41, wherein the acetate binding capacity is as determined by ion chromatography.
43. The MIP of embodiment 42, wherein the acetate binding capacity is as determined by ion chromatography as described in Section 4.3.

44. The MIP of any one of embodiments 1 to 43, which has greater affinity for acetate than chloride.
45. The MIP of embodiment 44, which has greater affinity for acetate than chloride as determined by ion chromatography.
46. The MIP of embodiment 45, which has a has greater affinity for acetate than chloride as determined by ion chromatography as described in Section 4.3.
47. The MIP of any one of embodiments 44 to 46, wherein the affinity for acetate is 10 to 100 times the affinity for chloride.
48. The MIP of embodiment 47, wherein the affinity for acetate is 10 to 50 times the affinity for chloride.
49. The MIP of embodiment 47, wherein the affinity for acetate is 10 to 20 times the affinity for chloride.
50. The MIP of embodiment 47, wherein the affinity for acetate is 25 to 100 times the affinity for chloride.
51. The MIP of embodiment 47, wherein the affinity for acetate is 25 to 50 times the affinity for chloride.
52. The MIP of embodiment 47, wherein the affinity for acetate is 50 to 100 times the affinity for chloride.
53. The MIP of embodiment 47, wherein the affinity for acetate is 75 to 100 times the affinity for chloride.
54. The MIP of any one of embodiments 5 to 53, wherein the functional molecules and secondary crosslinkers, when present, represent at least 80% of the dry weight of the MIP.
55. The MIP of embodiment 54, wherein the functional molecules and secondary crosslinkers, when present, represent at least 85% of the dry weight of the MIP.
56. The MIP of embodiment 54, wherein the functional molecules and secondary crosslinkers, when present, represent at least 90% of the dry weight of the MIP.
57. The MIP of embodiment 54, wherein the functional molecules and secondary crosslinkers, when present, represent at least 95% of the dry weight of the MIP.
58. The MIP of embodiment 54, wherein the functional molecules and secondary crosslinkers, when present, represent at least 97% of the dry weight of the MIP.
59. The MIP of embodiment 54, wherein the functional molecules and secondary crosslinkers, when present, represent at least 99% of the dry weight of the MIP.
60. A molecularly imprinted polymer (MIP) comprising one or more functional molecules, wherein at least 80 mol % of the functional molecules are functional crosslinkers.
61. The MIP of embodiment 60, wherein at least 85 mol % of the functional molecules are functional crosslinkers.
62. The MIP of embodiment 60, wherein at least 90 mol % of the functional molecules are functional crosslinkers.
63. The MIP of embodiment 60, wherein at least 95 mol % of the functional molecules are functional crosslinkers.
64. The MIP of embodiment 60, wherein at least 97 mol % of the functional molecules are functional crosslinkers.
65. The MIP of embodiment 60, wherein at least 99 mol % of the functional molecules are functional crosslinkers.
66. The MIP of embodiment 60, wherein the functional molecules consist essentially of or consist of functional crosslinkers.
67. The MIP of any one of embodiments 60 to 66, wherein the one or more functional molecules have been polymerized and crosslinked.
68. The MIP of any one of embodiments 60 to 67, wherein the one or more functional crosslinkers comprise one or more amide-containing crosslinkers.
69. The MIP of embodiment 68, wherein the one or more functional crosslinkers comprise or consist of N,N'-methylenebis(acrylamide) (MBA).
70. The MIP of any one of embodiments 60 to 69, wherein the one or more functional crosslinkers comprise one or more urea-containing crosslinkers.
71. The MIP of embodiment 70, wherein the one or more functional crosslinkers comprise or consist of 1,3-bis(4-vinylphenyl)urea, 1,3-bis(4-(allyloxy)phenyl)urea, 1,3-diallylurea, or a combination thereof.
72. The MIP of any one of embodiments 60 to 71, which comprises the one or more functional molecules and one or more secondary crosslinkers.
73. The MIP of embodiment 72, wherein the one or more secondary crosslinkers comprise or consist of ethylene glycol dimethacrylate (EGDA), ethylene glycol diacrylate, 1,2-diallyloxybenzene, divinylbenzene, 1,3-diisopropenylbenzene, divinylsuccinate, 1,3-divinyltetramethyldisiloxane, tri(ethylene glycol) divinyl ether, di(ethylene glycol) divinyl ether, trimethylolpropane trimethacrylate, pentaerythritol triacrylate, or a combination thereof.
74. The MIP of embodiment 73, wherein the one or more secondary crosslinkers comprises or consists of EGDA.
75. The MIP of any one of embodiments 72 to 74, wherein the molar ratio of the functional crosslinkers to secondary crosslinkers is 1:5 to 5:1.
76. The MIP of any one of embodiments 60 to 75, wherein the functional molecules and secondary crosslinkers, when present, represent at least 80% of the dry weight of the MIP.
77. The MIP of embodiment 76, wherein the functional molecules and secondary crosslinkers, when present, represent at least 85% of dry weight of the MIP.
78. The MIP of embodiment 76, wherein the functional molecules and secondary crosslinkers, when present, represent at least 90% of the dry weight of the MIP.
79. The MIP of embodiment 76, wherein the functional molecules and secondary crosslinkers, when present, represent at least 95% of the dry weight of the MIP.
80. The MIP of embodiment 76, wherein the functional molecules and secondary crosslinkers, when present, represent at least 97% of the dry weight of the MIP.
81. The MIP of embodiment 76, wherein the functional molecules and secondary crosslinkers, when present, represent at least 99% of the dry weight of the MIP.
82. The MIP of any one of embodiments 60 to 81, which is capable of binding a target molecule which is a metabolite derived from gut microbiota.
83. The MIP of any one of embodiments 60 to 82, which is capable of binding a target molecule which is a toxin.
84. The MIP of any one of embodiments 60 to 83, which is capable of binding a target molecule which is a short chain fatty acid, a bile acid, a vitamin, an enzyme cofactor, an amino acid, amino acid derivative, or a peptide.
85. The MIP of embodiment 84, which is capable of binding a target molecule which is a short chain fatty acid.
86. The MIP of embodiment 85, which is capable of binding one or more of acetate, propionate, and butyrate.
87. The MIP of embodiment 86, which is capable of binding acetate.

88. The MIP of embodiment 87, wherein the MIP in water has an acetate binding capacity of at least 5 mg of acetate per g of MIP.
89. The MIP of embodiment 88, wherein the MIP in water has an acetate binding capacity from 5 mg of acetate per g of MIP to 40 mg of acetate per g of MIP.
90. The MIP of embodiment 88 or embodiment 89, wherein the MIP in water has an acetate binding capacity of at least 10 mg of acetate per g of MIP.
91. The MIP of embodiment 88 or embodiment 89, wherein the MIP in water has an acetate binding capacity of at least 20 mg of acetate per g of MIP.
92. The MIP of embodiment 88 or embodiment 89, wherein the MIP in water has an acetate binding capacity of at least 30 mg of acetate per g of MIP.
93. The MIP of embodiment 88 or embodiment 89, wherein the MIP in water has an acetate binding capacity of at least 35 mg of acetate per g of MIP.
94. The MIP of any one of embodiments 88 to 93, wherein the binding capacity is as determined by ion chromatography.
95. The MIMP of embodiment 94, wherein the acetate binding capacity is as determined by ion chromatography as described in Section 4.3.
96. The MIP of any one of embodiments 88 to 95, which has greater affinity for acetate than chloride as determined by ion chromatography.
97. The MIP of embodiment 96, which has greater affinity for acetate than chloride as determined by ion chromatography as described in Section 4.3.
98. The MIP of embodiment 96 or embodiment 97, wherein the affinity for acetate is 10 to 100 times the affinity for chloride.
99. The MIP of embodiment 98, wherein the affinity for acetate is 10 to 50 times the affinity for chloride.
100. The MIP of embodiment 98, wherein the affinity for acetate is 10 to 20 times the affinity for chloride.
101. The MIP of embodiment 98, wherein the affinity for acetate is 25 to 100 times the affinity for chloride.
102. The MIP of embodiment 98, wherein the affinity for acetate is 25 to 50 times the affinity for chloride.
103. The MIP of embodiment 98, wherein the affinity for acetate is 50 to 100 times the affinity for chloride.
104. The MIP of embodiment 98, wherein the affinity for acetate is 75 to 100 times the affinity for chloride.
105. A preparation comprising a population of MIP particles according to any one of embodiments 1 to 104.
106. The preparation of embodiment 105, wherein the MIP particles in the preparation have a D (v, 0.5) particle size from 10 µm to 50 µm.
107. The preparation of embodiment 105, wherein the MIP particles in the preparation have a D (v, 0.5) particle size from 10 µm to 40 µm.
108. The preparation of embodiment 105, wherein the MIP particles in the preparation have a D (v, 0.5) particle size from 10 µm to 30 µm.
109. The preparation of embodiment 105, wherein the MIP particles in the preparation have a D (v, 0.5) particle size from 10 µm to 20 µm.
110. The preparation of embodiment 105, wherein the MIP particles in the preparation have a D (v, 0.5) particle size from 15 µm to 50 µm.
111. The preparation of embodiment 105, wherein the MIP particles in the preparation have a D (v, 0.5) particle size from 15 µm to 40 µm.
112. The preparation of embodiment 105, wherein the MIP particles in the preparation have a D (v, 0.5) particle size from 15 µm to 30 µm.
113. The preparation of embodiment 105, wherein the MIP particles in the preparation have a D (v, 0.5) particle size from 15 µm to 25 µm.
114. The preparation of embodiment 105, wherein the MIP particles in the preparation have a D (v, 0.5) particle size from 15 µm to 20 µm.
115. The preparation of embodiment 105, wherein the MIP particles in the preparation have a D (v, 0.5) particle size from 20 µm to 50 µm.
116. The preparation of embodiment 105, wherein the MIP particles in the preparation have a D (v, 0.5) particle size from 20 µm to 40 µm.
117. The preparation of embodiment 105, wherein the MIP particles in the preparation have a D (v, 0.5) particle size from 20 µm to 30 µm.
118. The preparation of embodiment 105, wherein the MIP particles in the preparation have a D (v, 0.5) particle size from 30 µm to 50 µm.
119. The preparation of embodiment 105, wherein the MIP particles in the preparation have a D (v, 0.5) particle size from 30 µm to 40 µm.
120. The preparation of embodiment 105, wherein the MIP particles in the preparation have a D (v, 0.5) particle size from 40 µm to 50 µm.
121. The preparation of any one of embodiments 105 to 120, wherein the D (v, 0.5) particle size is as measured by a laser particle size analyzer.
122. The preparation of any one of embodiments 105 to 121, wherein the preparation is at least 85% pure.
123. The preparation of embodiment 122, wherein the preparation is 85% to 99% pure.
124. The preparation of embodiment 122, wherein the preparation is 85% to more than 99% pure.
125. The preparation of embodiment 122, wherein the preparation is 85% to more than 99.5% pure.
126. The preparation of embodiment 122, wherein the preparation is 85% to more than 99.8% pure.
127. The preparation of any one of embodiments 122 to 126, wherein the preparation is at least 90% pure.
128. The preparation of any one of embodiments 122 to 126, wherein the preparation is at least 95% pure.
129. The preparation of any one of embodiments 122 to 126, wherein the preparation is at least 96% pure.
130. The preparation of any one of embodiments 122 to 126, wherein the preparation is at least 97% pure.
131. The preparation of any one of embodiments 122 to 126, wherein the preparation is at least 98% pure.
132. The preparation of any one of embodiments 122 to 126, wherein the preparation is at least 99% pure.
133. The preparation of any one of embodiments 122 to 132, wherein the purity is purity determined by IR spectroscopy.
134. A process for making the MIP of any one of embodiments 5 to 59, comprising polymerizing and crosslinking a mixture comprising the one or more functional molecules and one or more template molecules.
135. The process of embodiment 134, wherein the molar ratio of the one or more functional molecules to the one or more template molecules is 1:1 to 15:1.
136. The process of embodiment 135, wherein the molar ratio of the one or more functional molecules to the one or more template molecules is 1:1 to 5:1.

137. The process of embodiment 136, wherein the molar ratio of the one or more functional molecules to the one or more template molecules is 3:1 to 4:1.

138. The process of embodiment 137, wherein the molar ratio of the one or more functional molecules to the one or more template molecules is 3:1.

139. The process of embodiment 137, wherein the molar ratio of the one or more functional molecules to the one or more template molecules is 4:1.

140. A process for making the MIP of any one of embodiments 60 to 104, comprising polymerizing and crosslinking a mixture comprising the one or more functional molecules and one or more template molecules.

141. The process of embodiment 140, wherein the molar ratio of the one or more functional crosslinkers to the one or more template molecules is 1:1 to 15:1.

142. The process of embodiment 141, wherein the molar ratio of the one or more functional molecules to the one or more template molecules is 1:1 to 5:1.

143. The process of embodiment 142, wherein the molar ratio of the one or more functional molecules to the one or more template molecules is 3:1 to 4:1.

144. The process of embodiment 143, wherein the molar ratio of the one or more functional molecules to the one or more template molecules is 3:1.

145. The process of embodiment 143, wherein the molar ratio of the one or more functional molecules to the one or more template molecules is 4:1.

146. The process of any one of embodiments 140 to 145, wherein the one or more template molecules comprise one or more target molecules, and/or one or more salts thereof.

147. A process for making the MIP of any one of embodiments 87 to 104, comprising polymerizing and crosslinking a mixture comprising the one or more functional molecules and one or more template molecules.

148. The process of embodiment 147, wherein the molar ratio of the one or more functional crosslinkers to the one or more template molecules is 1:1 to 15:1.

149. The process of embodiment 148, wherein the molar ratio of the one or more functional molecules to the one or more template molecules is 1:1 to 5:1.

150. The process of embodiment 149, wherein the molar ratio of the one or more functional molecules to the one or more template molecules is 3:1 to 4:1.

151. The process of embodiment 149, wherein the molar ratio of the one or more functional molecules to the one or more template molecules is 3:1.

152. The process of embodiment 149, wherein the molar ratio of the one or more functional molecules to the one or more template molecules is 4:1.

153. The process of any one of embodiments 122-139 or 147-152, wherein the one or more template molecules comprise one or more short chain fatty acids and/or one or more salts thereof.

154. The process of any one of embodiments 122-139 or 147-152, wherein the one or more template molecules comprise acetate and/or one or more salts thereof, propionate and/or one or more salts thereof, isobutyrate and/or one or more salts thereof, butyrate and/or one or more salts thereof, pivalate and/or one or more salts thereof, benzoate and/or one or more salts thereof, malonate and/or one or more salts thereof, succinate and/or one or more salts thereof, bicarbonate and/or one or more salts thereof, or carbonate and/or one or more salts thereof.

155. The process of embodiment 154, wherein the one or more template molecules comprise acetate and/or one or more salts thereof.

156. The process of embodiment 155, wherein the one or more template molecules comprise an acetate salt.

157. The process of embodiment 156, wherein the acetate salt comprises potassium acetate and/or sodium acetate.

158. The process of embodiment 157, wherein the acetate salt is potassium acetate.

159. The process of embodiment 157, wherein the acetate salt is a sodium acetate.

160. The process of embodiment 154, wherein the one or more template molecules comprise propionate and/or one or more salts thereof.

161. The process of embodiment 154, wherein the one or more template molecules comprise isobutyrate and/or one or more salts thereof.

162. The process of embodiment 154, wherein the one or more template molecules comprise butyrate and/or one or more salts thereof.

163. The process of embodiment 154, wherein the one or more template molecules comprise pivalate and/or one or more salts thereof.

164. The process of embodiment 154, wherein the one or more template molecules comprise benzoate and/or one or more salts thereof.

165. The process of embodiment 154, wherein the one or more template molecules comprise malonate and/or one or more salts thereof.

166. The process of embodiment 154, wherein the one or more template molecules comprise succinate and/or one or more salts thereof.

167. The process of embodiment 154, wherein the one or more template molecules comprise bicarbonate and/or one or more salts thereof.

168. The process of embodiment 154, wherein the one or more template molecules comprise carbonate and/or one or more salts thereof.

169. The process of any one of embodiments 122 to 168, when depending directly or indirectly from embodiment 19 or embodiment 72, wherein the mixture further comprises the one or more secondary crosslinkers.

170. The process of any one of embodiments 122 to 169, wherein the mixture comprises one or more solvents.

171. The process of embodiment 170, wherein the one or more solvents comprises methanol (MeOH).

172. The process of any one of embodiments 122 to 171, which further comprises forming the mixture.

173. The process of any one of embodiments 122 to 172, which further comprises degassing the mixture prior to polymerization.

174. The process of embodiment 173, wherein the degassing comprises bubbling an inert gas through the mixture.

175. The process of embodiment 174, wherein the gas is nitrogen or argon.

176. The process of any one of embodiments 173 to 175, wherein the temperature of the mixture during degassing is 60° C. to 80° C.

177. The process of any one of embodiments 122 to 176, wherein the temperature of the mixture during polymerization is 60° C. to 80° C.

178. The process of any one of embodiments 122 to 169, wherein the polymerization is initiated by an initiator.

179. The process of embodiment 178, wherein the initiator comprises a photoinitiator or thermal initiator.
180. The process of embodiment 179, wherein the initiator comprises potassium persulfate, sodium persulfate, ammonium persulfate, 2,2'-azobis(2-methylpropionate) (V601), 2,2'-azobisisobutyronitrile (AIBN), benzoyl peroxide, t-butyl peroxide, t-butyl hydroperoxide, acetyl peroxide, 2-hydroxy-4'-(2-hydroxyethoxy)-2-methylpropiophenone, or a combination thereof.
181. The process of embodiment 180, wherein the initiator comprises ammonium persulfate.
182. The process of any one of embodiments 122 to 181, further comprising washing the MIP to remove the one or more template molecules.
183. The process of embodiment 182, wherein the washing comprises washing the MIP with one or more solvents.
184. The process of embodiment 183, which comprises sequentially washing the MIP with more than one solvent.
185. The process of embodiment 184, which comprises sequentially washing the MIP with methanol, water, and ethanol.
186. The process of any one of embodiments 183 to 185, wherein the washing comprising performing Soxhlet extraction.
187. The process of any one of embodiments 122 to 186, further comprising drying the MIP.
188. The process of any one of embodiments 122 to 187, further comprising crushing or grinding the MIP.
189. The process of any one of embodiments 122 to 188, further comprising selecting MIP particles having a desired size.
190. The process of embodiment 189, wherein selecting MIP particles having a desired size comprises filtering the MIP through one or more sieves.
191. The process of embodiment 190, wherein the one or more sieves comprise a 300 mesh sieve, a 500 mesh sieve, a 900 mesh sieve, an 1800 mesh sieve, or a combination thereof.
192. The process of embodiment 191, wherein the one or more sieves comprise a 300 mesh sieve, a 500 mesh sieve, a 900 mesh sieve, and an 1800 mesh sieve.
193. The process of any one of embodiments 189 to 191, which comprises selecting MIP particles having a D (v, 0.5) particle size of 50 μm or less.
194. The process of embodiment 193, which comprises selecting MIP particles having a D (v, 0.5) particle size from 10 μm to 50 μm.
195. The process of embodiment 194, which comprises selecting MIP particles having a D (v, 0.5) particle size from 10 μm to 40 μm.
196. The process of embodiment 194, which comprises selecting MIP particles having a D (v, 0.5) particle size from 10 μm to 30 μm.
197. The process of embodiment 194, which comprises selecting MIP particles having a D (v, 0.5) particle size from 10 μm to 20 μm.
198. The process of embodiment 194, which comprises selecting MIP particles having a D (v, 0.5) particle size from 15 μm to 50 μm.
199. The process of embodiment 194, which comprises selecting MIP particles having a D (v, 0.5) particle size from 15 μm to 40 μm.
200. The process of embodiment 194, which comprises selecting MIP particles having a D (v, 0.5) particle size from 15 μm to 30 μm.
201. The process of embodiment 194, which comprises selecting MIP particles having a D (v, 0.5) particle size from 15 μm to 25 μm.
202. The process of embodiment 194, which comprises selecting MIP particles having a D (v, 0.5) particle size from 15 μm to 20 μm.
203. The process of embodiment 194, which comprises selecting MIP particles having a D (v, 0.5) particle size from 20 μm to 50 μm.
204. The process of embodiment 194, which comprises selecting MIP particles having a D (v, 0.5) particle size from 20 μm to 40 μm.
205. The process of embodiment 194, which comprises selecting MIP particles having a D (v, 0.5) particle size from 20 μm to 30 μm.
206. The process of embodiment 194, which comprises selecting MIP particles having a D (v, 0.5) particle size from 30 μm to 50 μm.
207. The process of embodiment 194, which comprises selecting MIP particles having a D (v, 0.5) particle size from 30 μm to 40 μm.
208. The process of embodiment 194, which comprises selecting MIP particles having a D (v, 0.5) particle size from 40 μm to 50 μm.
209. The process of any one of embodiments 193 to 208, wherein the D (v, 0.5) particle size is as measured by a laser particle size analyzer.
210. A MIP produced by the process of any one of embodiments 122 to 209.
211. A preparation comprising a population of MIP particles produced by the process of any one of embodiments 122 to 209.
212. A pharmaceutical composition comprising (i) the MIP of any one of embodiments 1 to 104 or 210 or a preparation of any one of embodiments 105 to 133 or 211 and (ii) a pharmaceutically acceptable excipient.
213. The pharmaceutical composition of embodiment 212, which is formulated for oral administration.
214. The pharmaceutical composition of embodiment 213, which is a liquid. 215. The pharmaceutical composition of embodiment 214, which is a suspension. 216. The pharmaceutical composition of embodiment 214, which is a solution.
217. The pharmaceutical composition of any one of embodiments 214 to 216, wherein the excipient comprises water, saline, ethanol, propylene glycol, 1,3-butyleneglycol, an oil, glycerol, a polyethylene glycol, or a combination of any of the foregoing.
218. The pharmaceutical composition of embodiment 213, which is a solid.
219. The pharmaceutical composition of embodiment 218, wherein the excipient comprises one or more starches, lactose, dextrose, sucrose, glucose, mannitol, silicic acid, carboxymethylcellulose, an alginate, gelatin, polyvinylpyrrolidone, sucrose, acacia, agar-agar, calcium carbonate, talc, calcium stearate, magnesium stearate, a solid polyethylene glycol, sodium lauryl sulfate, or a combination of any of the foregoing.
220. The pharmaceutical composition of embodiment 218 or embodiment 219, which is a capsule.
221. The pharmaceutical composition of embodiment 218 or embodiment 219, which is a tablet.
222. The pharmaceutical composition of embodiment 218 or embodiment 219, which is a powder.

223. The pharmaceutical composition of embodiment 218 or embodiment 219, which is a granule.
224. The pharmaceutical composition of embodiment 218 or embodiment 219, which is an oral strip.
225. The pharmaceutical composition of embodiment 218 or embodiment 219, which is a chewing gum.
226. The pharmaceutical composition of embodiment 218 or embodiment 219, which is a troche.
227. A method of sequestering acetate in the gastrointestinal tract of a subject comprising orally administering to the subject an effective amount of a molecularly imprinted polymer (MIP) capable of binding acetate.
228. A method of treating a subject diagnosed with or at risk of a condition associated with accumulation of acetate comprising administering to the subject an effective amount of a molecularly imprinted polymer (MIP) capable of binding acetate.
229. The method of embodiment 228, wherein the condition associated with accumulation of acetate comprises metabolic syndrome.
230. The method of embodiment 228, wherein the condition associated with accumulation of acetate comprises obesity.
231. A method of reducing the body weight of a subject comprising orally administering to the subject an effective amount of a molecularly imprinted polymer (MIP) capable of binding acetate.
232. The method of any one of embodiments 227 to 231, which comprises administering to the subject an acetate-binding MIP according to any one of embodiments 1 to 104 or 210, a preparation according to any one of embodiments 105 to 133 or 211, or a pharmaceutical composition according to any one of embodiments 212 to 226 (or solution or suspension made from the pharmaceutical composition) which comprises an acetate-binding MIP.
233. A method of sequestering a target molecule in the gastrointestinal tract of a subject comprising administering to the subject an effective amount of a molecularly imprinted polymer (MIP) according to any one of embodiments 1 to 104 or 210 that binds the target molecule, a preparation according to any one of embodiments 105 to 133 or 211 comprising a MIP that binds the target molecule, or a pharmaceutical composition according to any one of embodiments 212 to 226 (or solution or suspension made from the pharmaceutical composition) which comprises a MIP that binds the target molecule.
234. A method of treating a subject diagnosed with or at risk of a condition associated with accumulation of a target molecule, comprising administering to the subject an effective amount of molecularly imprinted polymer (MIP) of any one of embodiments 1 to 104 or 210 that binds the target molecule, a preparation of any one of embodiments 105 to 133 or 211 comprising a MIP that binds the target molecule, or a pharmaceutical composition according to any one of embodiments 212 to 226 (or solution or suspension made from the pharmaceutical composition) which comprises a MIP that binds the target molecule.
235. The method of any one of embodiments 227 to 234, wherein the MIP, preparation, or pharmaceutical composition (or solution or suspension made from the pharmaceutical composition) is administered orally.
236. The method of any one of embodiments 227 to 235, which comprises administering the MIP mixed with food.
237. The method of any one of embodiments 227 to 236, wherein the subject is administered 100 mg to 500 g of the MIP per day.
238. The method of embodiment 237, wherein the subject is administered 100 mg to 1 g of the MIP per day.
239. The method of embodiment 237, wherein the subject is administered 1 g to 5 g of the MIP per day.
240. The method of embodiment 237, wherein the subject is administered 1 g to 10 g of the MIP per day.
241. The method of embodiment 237, wherein the subject is administered 5 g to 15 g of the MIP per day.
242. The method of embodiment 237, wherein the subject is administered 10 g to 25 g of the MIP per day.
243. The method of embodiment 237, wherein the subject is administered, 20 g to 50 g of the MIP per day.
244. The method of embodiment 237, wherein the subject is administered 20 g to 100 g of the MIP per day.
245. The method of embodiment 237, wherein the subject is administered 50 g to 100 g of the MIP per day.
246. The method of embodiment 237, wherein the subject is administered 50 g to 200 g of the MIP per day.
247. The method of embodiment 237, wherein the subject is administered 100 g to 200 g of the MIP per day.
248. The method of embodiment 237, wherein the subject is administered 100 g to 500 g of the MIP per day.
249. The method of embodiment 237, wherein the subject is administered 200 g to 500 g of the MIP per day.
250. The method of embodiment 237, wherein the subject is administered 300 g to 500 g of the MIP per day.

7. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A molecularly imprinted polymer (MIP) capable of binding acetate, the MIP comprising (i) functional molecules comprising N,N'-methylenebis(acrylamide) (MBA) and (ii) ethylene glycol dimethacrylate (EGDA), wherein the molar ratio of N,N'-methylenebis(acrylamide) (MBA) to ethylene glycol dimethacrylate (EGDA) is 1:1 to 4:5.
2. The MIP of claim 1, which is capable of binding acetate in a human gastrointestinal tract.
3. The MIP of claim 1, wherein at least 80 mol % of the functional molecules in the MIP are functional crosslinkers.
4. The MIP of claim 3, wherein at least 90 mol % of the functional molecules in the MIP are functional crosslinkers.
5. The MIP of claim 3, wherein at least 95 mol % of the functional molecules in the MIP are functional crosslinkers.
6. The MIP of claim 3, wherein at least 97 mol % of the functional molecules in the MIP are functional crosslinkers.
7. The MIP of claim 3, wherein at least 99 mol % of the functional molecules in the MIP are functional crosslinkers.
8. The MIP of claim 1, wherein the MIP in water has an acetate binding capacity from 5 mg of acetate per g of MIP to 40 mg of acetate per g of MIP.
9. The MIP of claim 1, which has greater affinity for acetate than chloride.

10. The MIP of claim 1, which has a D (v, 0.5) particle size from 10 μm to 50 μm.

11. The MIP of claim 10, which has a D (v, 0.5) particle size from 10 μm to 50-40 μm.

12. The MIP of claim 11, wherein the MIP has a D (v, 0.5) particle size from 15 μm to 25 μm.

13. The MIP of claim 1, wherein the molar ratio of N,N'-methylenebis(acrylamide) (MBA) to ethylene glycol dimethacrylate (EGDA) is 1:1.

14. The MIP of claim 13, which has greater affinity for acetate than chloride.

15. The MIP of claim 1, wherein the MIP comprises MBA N,N'-methylenebis(acrylamide) (MBA) and ethylene glycol dimethacrylate (EGDA) that have been polymerized and crosslinked in the presence of one or more template molecules comprising acetate and/or a salt thereof.

16. The MIP of claim 15, wherein the one or more template molecules comprise potassium acetate.

17. The MIP of claim 1, wherein the MIP in water has an acetate binding capacity from 20 mg of acetate per g of MIP to 40 mg of acetate per g of MIP.

18. A method of treating a subject diagnosed with or at risk of a condition associated with accumulation of acetate comprising administering to the subject an effective amount of the MIP of claim 1.

19. The method of claim 18, wherein the condition associated with accumulation of acetate is obesity.

* * * * *